(12) United States Patent
Watt

(10) Patent No.: US 8,534,164 B2
(45) Date of Patent: Sep. 17, 2013

(54) SCREW DELIVERY SYSTEM

(75) Inventor: Philip Watt, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 234 days.

(21) Appl. No.: 12/956,295

(22) Filed: Nov. 30, 2010

(65) Prior Publication Data
US 2011/0130767 A1 Jun. 2, 2011

Related U.S. Application Data

(60) Provisional application No. 61/265,484, filed on Dec. 1, 2009.

(51) Int. Cl.
*B25B 23/06* (2006.01)
*A61B 17/56* (2006.01)

(52) U.S. Cl.
USPC .............................. 81/57.37; 81/434; 606/104

(58) Field of Classification Search
USPC ............. 81/431, 433, 434, 435, 57.23, 57.37; 606/104; 227/120
See application file for complete search history.

(56) References Cited

U.S. PATENT DOCUMENTS

| | | | |
|---|---|---|---|
| 2,202,240 A | 5/1940 | Trotter | |
| 3,528,466 A | 9/1970 | Tracy | |
| 4,936,169 A * | 6/1990 | Parsons | 81/57.37 |
| 4,998,452 A * | 3/1991 | Blum | 81/57.37 |
| 5,302,068 A | 4/1994 | Janusz et al. | |
| 5,445,641 A | 8/1995 | Frigg et al. | |
| 5,735,854 A | 4/1998 | Caron et al. | |
| 6,328,746 B1 | 12/2001 | Gambale | |
| 6,845,693 B1 * | 1/2005 | Babij, Jr. | 81/434 |
| 7,104,167 B2 * | 9/2006 | Babij, Jr. | 81/434 |
| 7,406,899 B2 | 8/2008 | Walker | |
| 7,461,574 B2 * | 12/2008 | Lewis et al. | 81/57.37 |
| 2004/0243139 A1 | 12/2004 | Lewis et al. | |
| 2006/0048366 A1 | 3/2006 | Goodhue et al. | |
| 2007/0106283 A1 | 5/2007 | Garcia et al. | |
| 2007/0119871 A1 | 5/2007 | Garcia | |
| 2008/0016989 A1 | 1/2008 | Walker | |
| 2010/0331852 A1* | 12/2010 | Neubardt | 606/104 |

FOREIGN PATENT DOCUMENTS

| | | |
|---|---|---|
| DE | 3200367 A1 | 7/1982 |
| EP | 0800796 A1 | 10/1997 |
| GB | 230189 | 3/1925 |

\* cited by examiner

*Primary Examiner* — David B Thomas
(74) *Attorney, Agent, or Firm* — Woodcock Washburn LLP

(57) ABSTRACT

A screw delivery system is provided. Such a system may include a carrier including a carrier body, a driver, and a nose. The carrier may define a bore that extends at least partially through the carrier body. The driver may be configured to be at least partially disposed in the bore. The driver may include a head that is configured to mate with a head of a fastener. At least a first guide member may be carried by the carrier body. The nose may be operably aligned with the bore, and may include at least a second guide member that is configured to engage the first guide member. The system may be configured such that insertion of the driver from the bore into the nose causes the first and second guide members to engage so as to cause the nose to rotate relative to the carrier body.

46 Claims, 23 Drawing Sheets

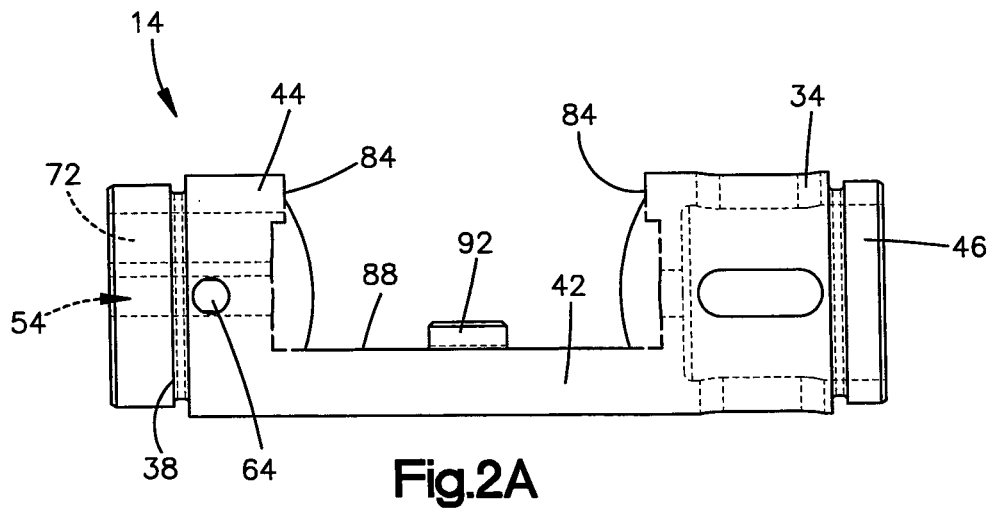
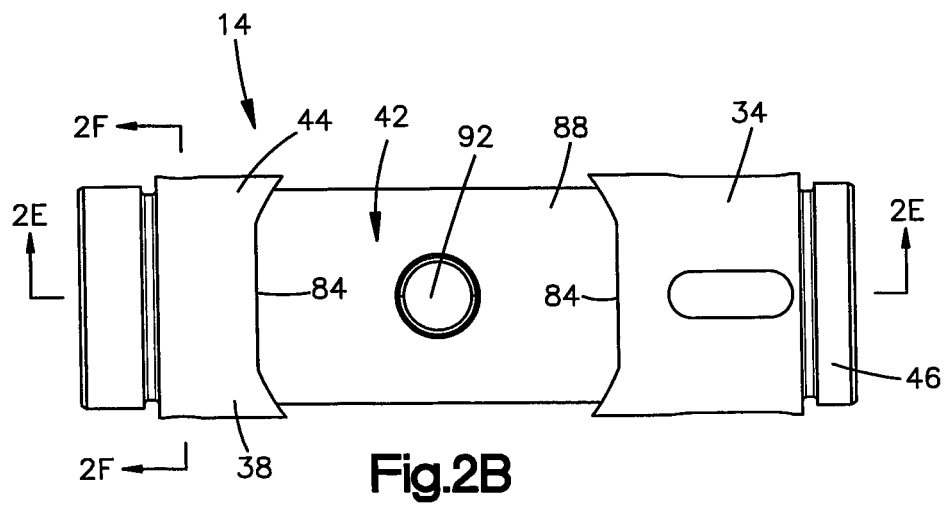
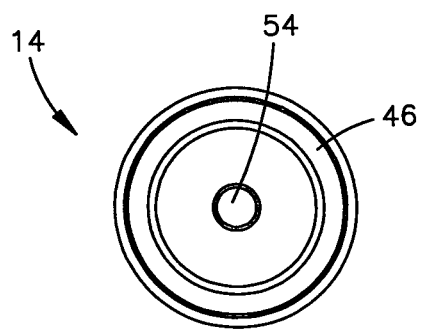
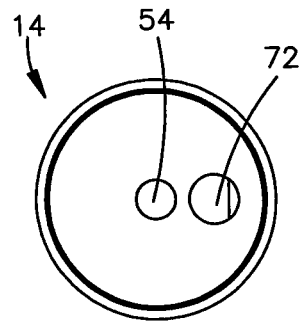

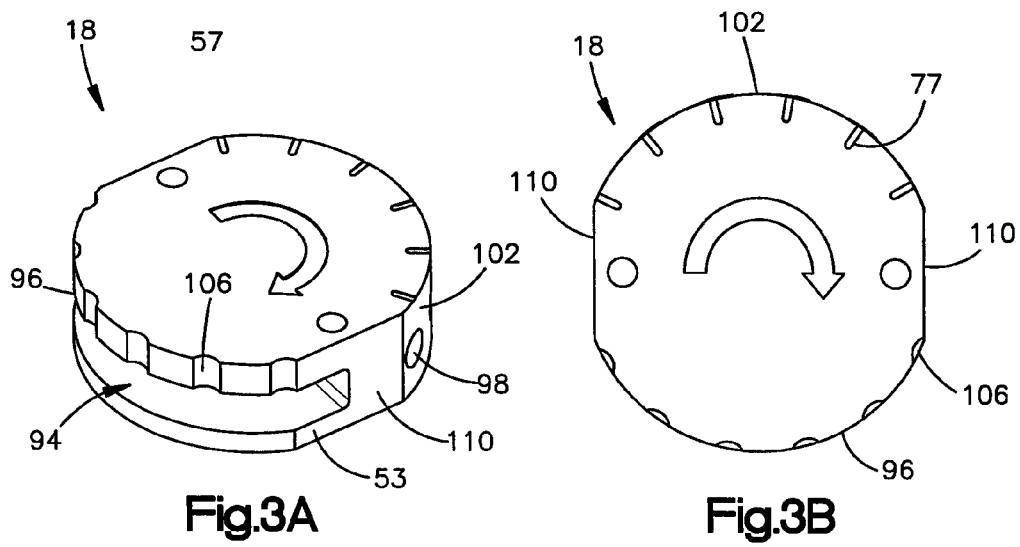
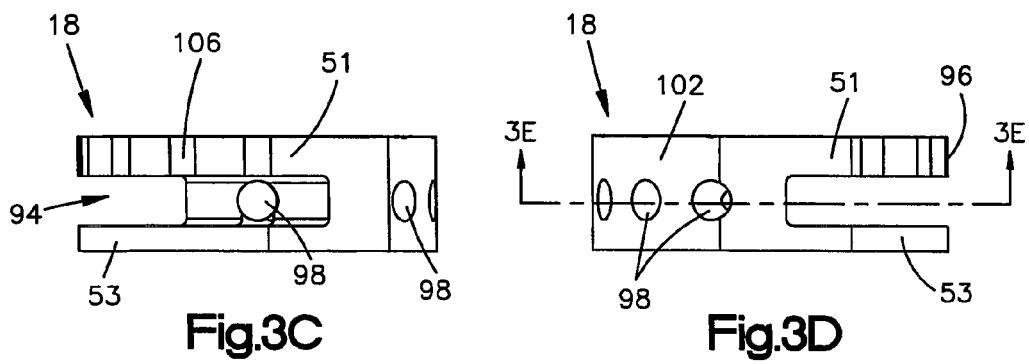
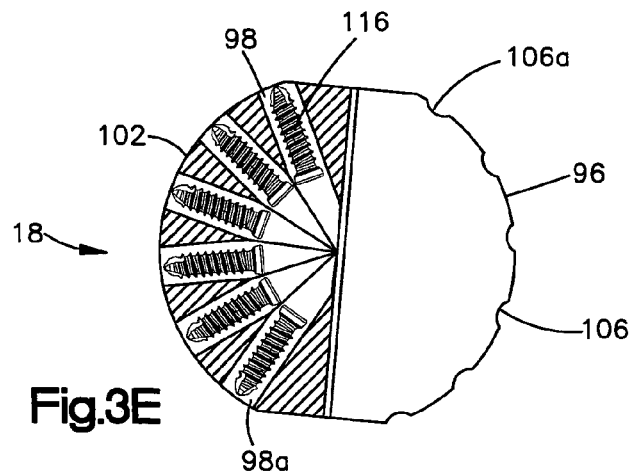

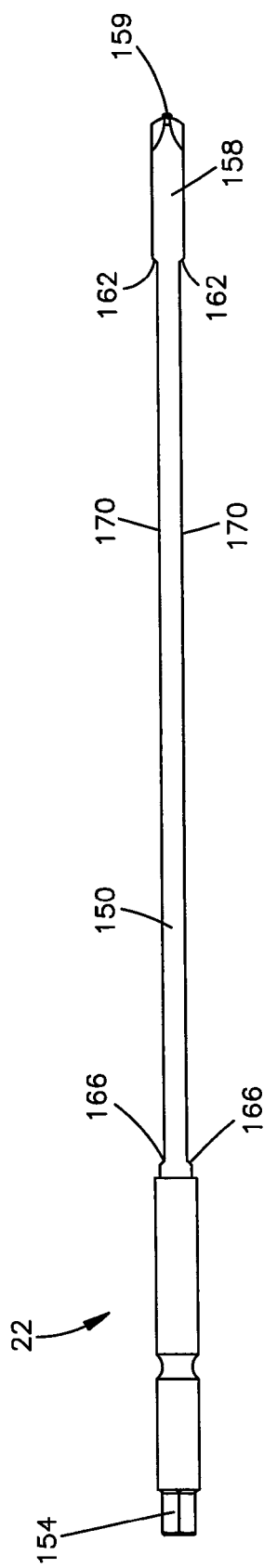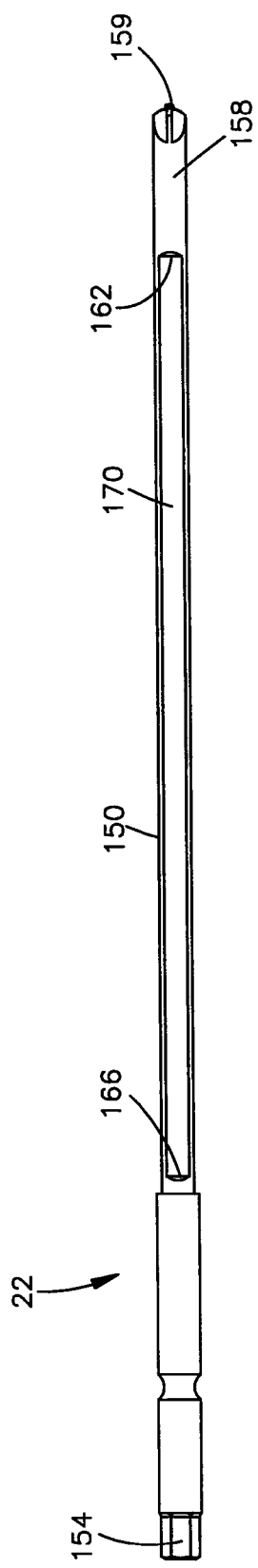

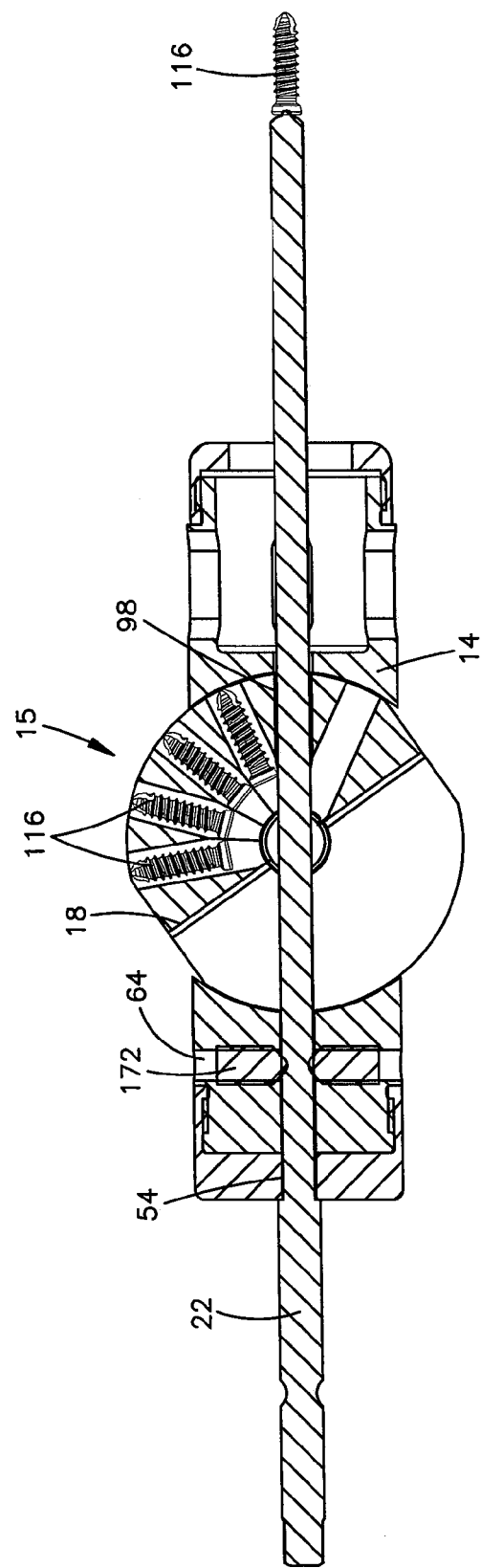

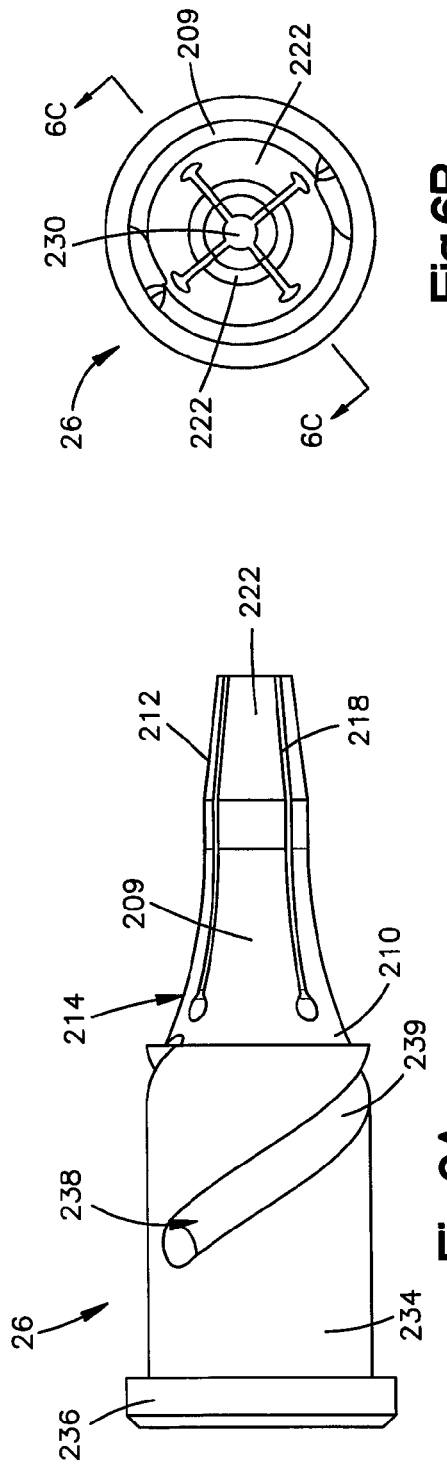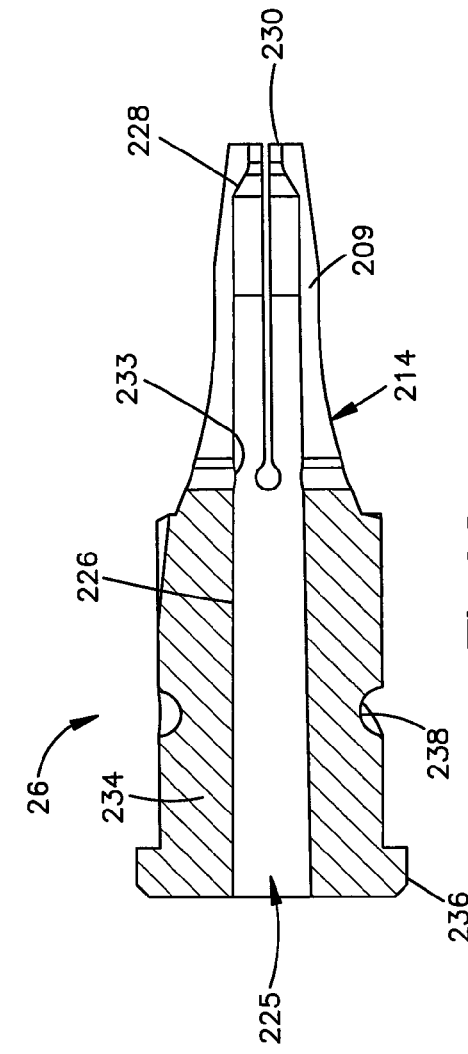

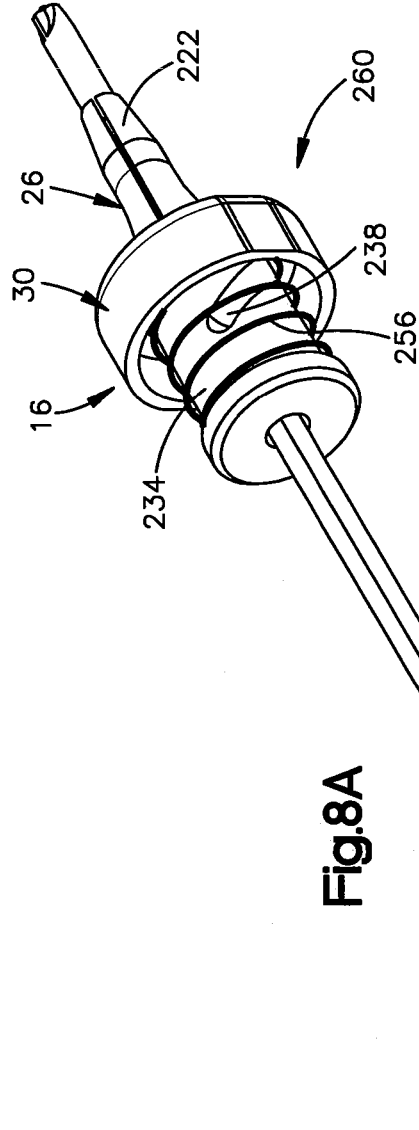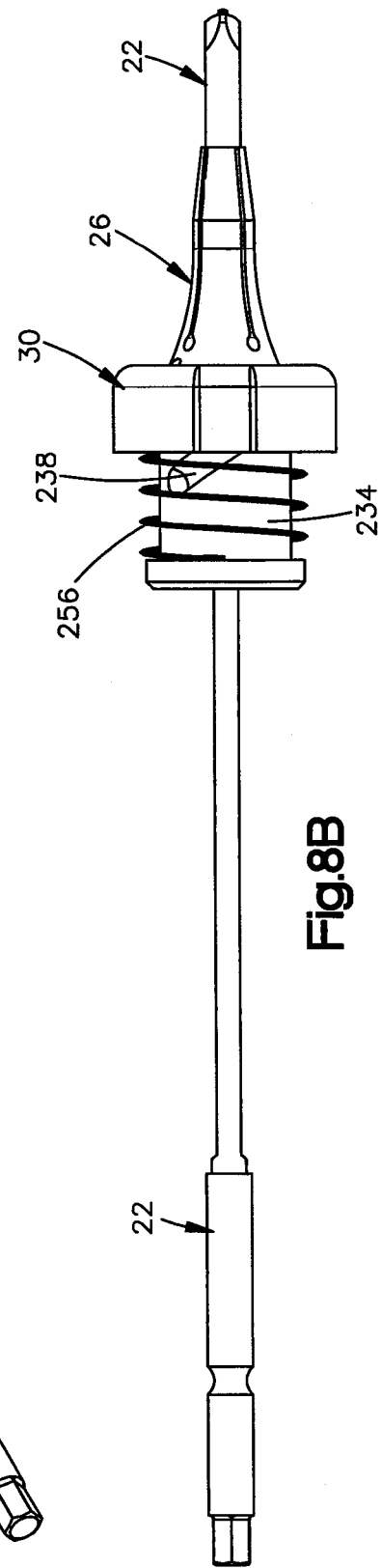

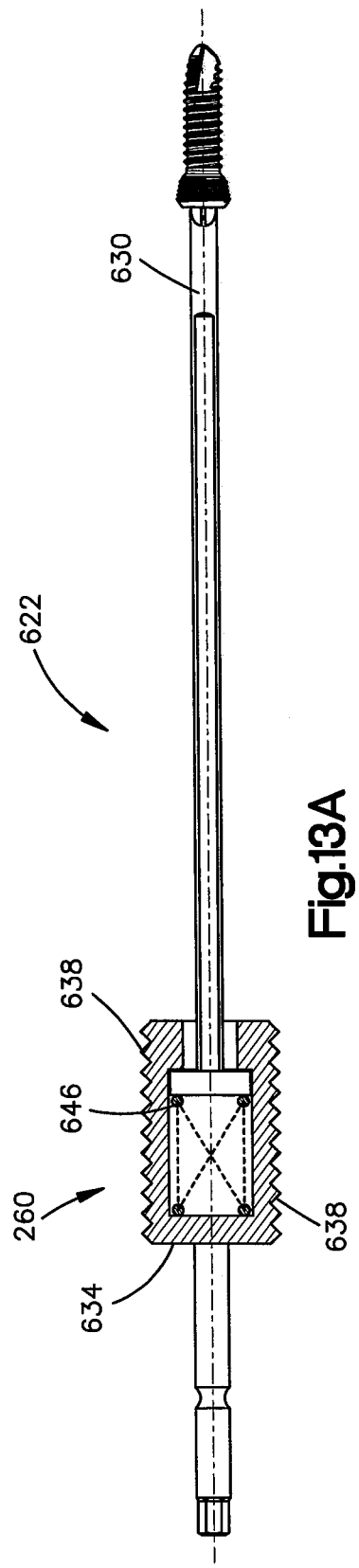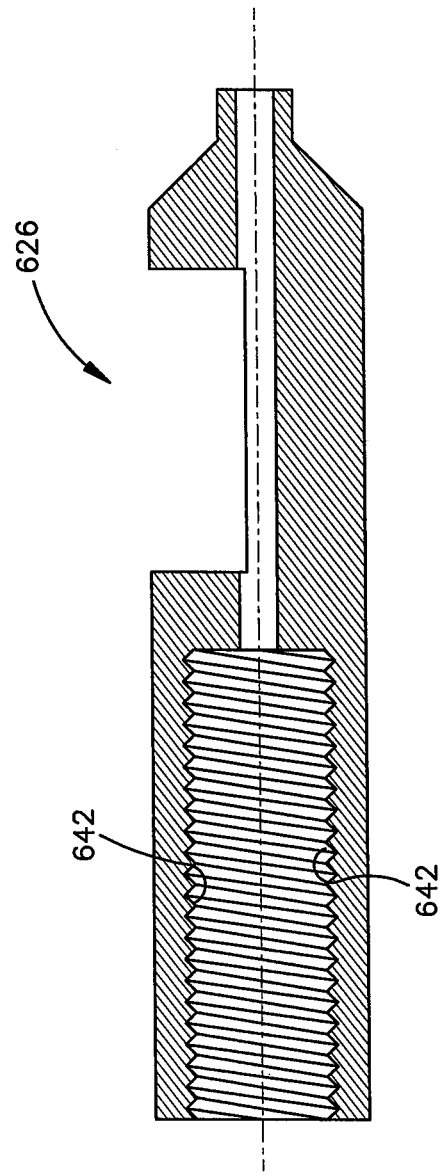
Fig.13A
Fig.13B

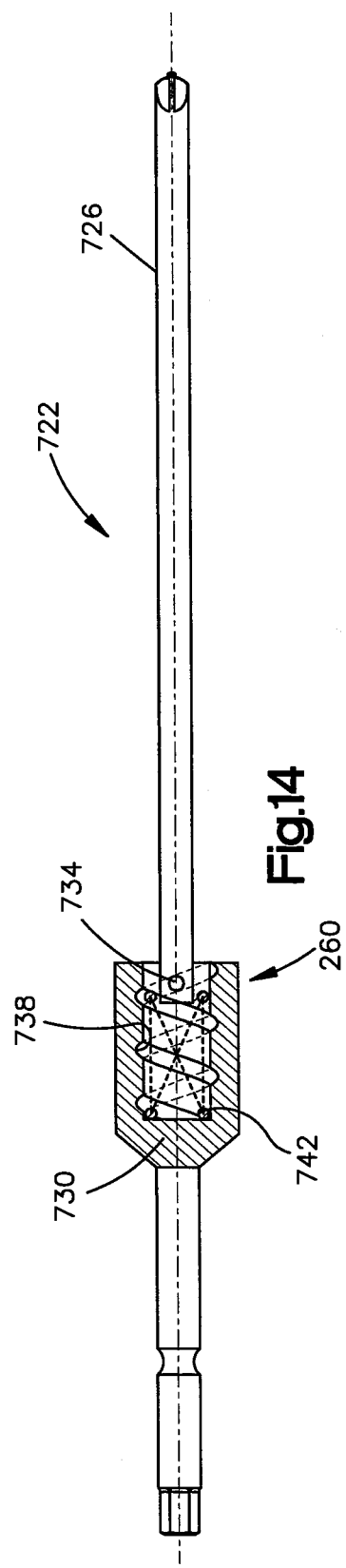

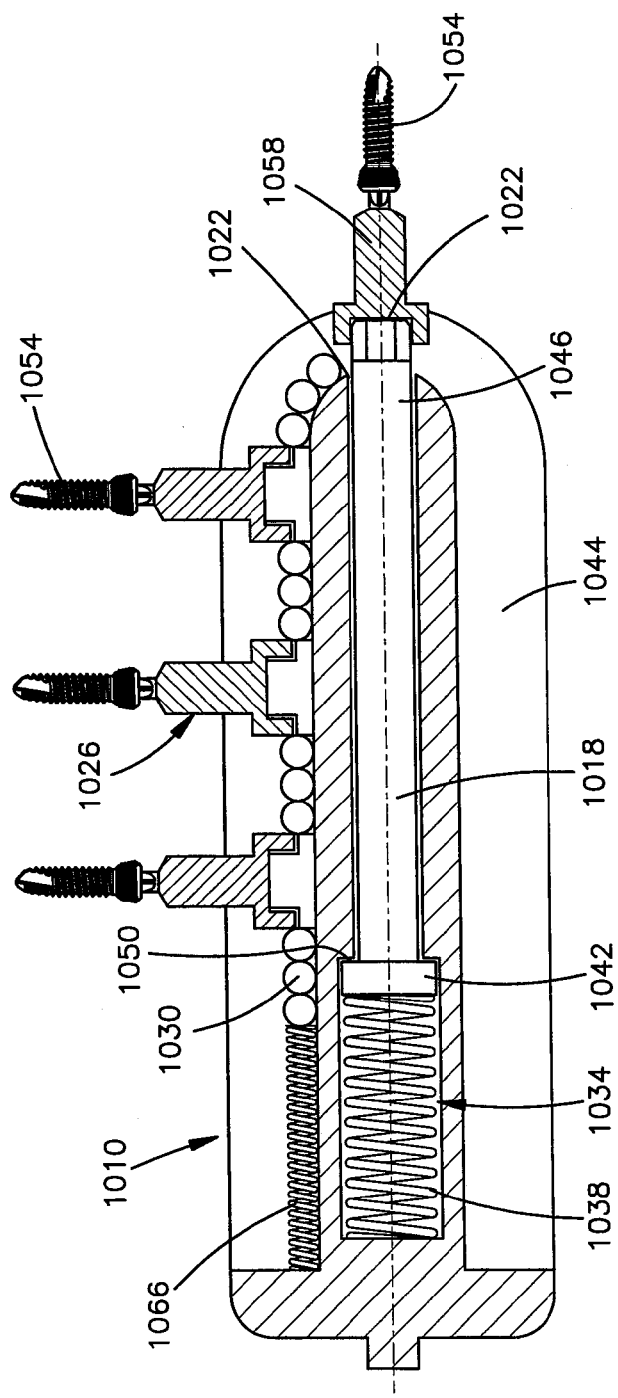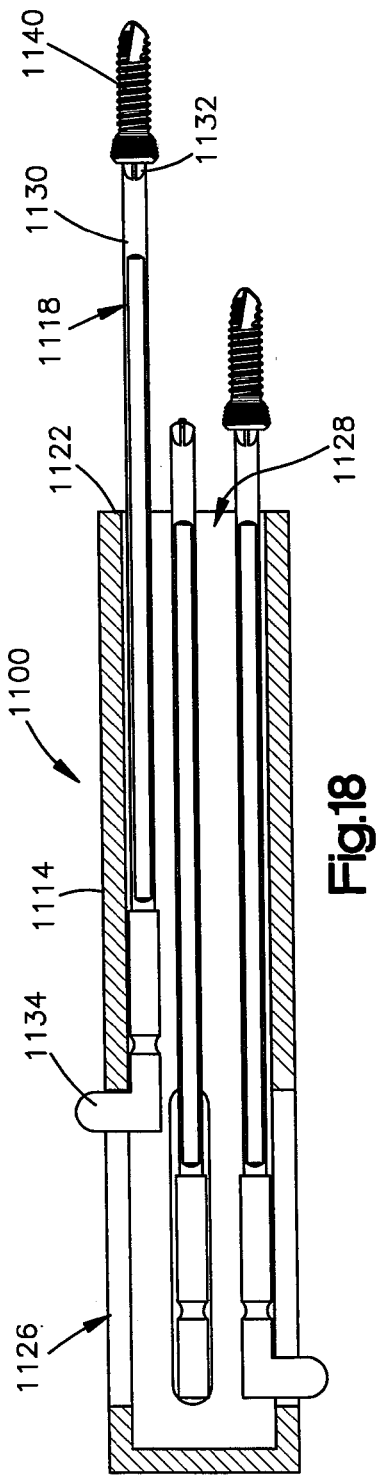

SCREW DELIVERY SYSTEM

CROSS-REFERENCE TO RELATED APPLICATIONS

This application claims priority to U.S. Provisional Patent Application Ser. No. 61/265,484, filed Dec. 1, 2009, the disclosure of which is hereby incorporated by reference as if set forth in its entirety herein.

BACKGROUND

Screws used to fix an implant to an underlying bone, for instance in craniofacial applications, are relatively small in order to maintain a low profile of the implant. Conventional drivers are configured to transfer torque to craniofacial screws sufficient to drive the screws into complementary screw holes of the implant. It has been found that cruciform drives are able to withstand the insertion torque associated with inserting the screws to a desired depth.

Currently, screws are held in modules so that their heads can be mated with the cruciform drive of a screw driver. During operation, the user aligns the screw driver to the screw, and a compressive force is applied to the screw driver to wedge the screw onto the screw driver. In many cases, the screw driver is pre-loaded by operating room personnel and passed to the surgeon for screw insertion. Multiple screw drivers are often used, so as to reduce the delay in fixing the implant to underlying bone. Unfortunately, this current technique can result in variation of either or both of alignment of the screw with the driver and the force used to wedge the screw onto the driver. Therefore, screws can fall off the driver because they care misaligned or not sufficiently wedged onto the screw driver. This may increase the duration of the surgical procedure, and become a nuisance for the user.

SUMMARY

In accordance with one embodiment, a screw delivery system includes a carrier including a carrier body, a driver, and a nose. The carrier may define a bore that extends at least partially through the carrier body. The driver may be configured to be at least partially disposed in the bore. The driver may include a head that is configured to mate with a head of a fastener. At least a first guide member may be carried by the carrier body. The nose may be operably aligned with the bore, and may include at least a second guide member that is configured to engage the first guide member. The system may be configured such that insertion of the driver from the bore into the nose causes the first and second guide members to engage so as to cause the nose to rotate relative to the carrier body.

In accordance with another embodiment, the screw delivery system may include a carrier, and a driver. The carrier may include a carrier body, and a bore that extends at least partially through the carrier body. The carrier body may be configured to hold a plurality of fasteners. The driver may be configured to be at least partially disposed in the bore, and may have a head that is configured to mate with a head of a fastener. The bore may be configured to selectively receive each fastener of the plurality of fasteners such that as the driver is advanced within the bore, the head of the driver is capable of directly engaging the head of each fastener when each fastener is to be driven.

In accordance with still another embodiment, a screw cartridge includes a cartridge body having a curved front face and a curved rear face joined by a pair of substantially flat side walls. The cartridge may further include a plurality of bores extending through at least a portion of the cartridge body, wherein each bore extends from the front face of the body and opens up to the rear face. In some embodiments a screw may be positioned within at least one of the bores.

BRIEF DESCRIPTION OF THE DRAWINGS

The foregoing summary, as well as the following detailed description of preferred embodiments of the application, will be better understood when read in conjunction with the appended drawings. For the purposes of illustrating the screw delivery system of the present application, there is shown in the drawings preferred embodiments. It should be understood, however, that the application is not limited to the precise systems shown. In the drawings:

FIG. 2A is a side elevation view of the carrier of the screw delivery system shown in FIG. 1A;

FIG. 2B is a top plan view of the carrier shown in FIG. 2A;

FIG. 2C is a front elevation view of the carrier shown in FIG. 2A;

FIG. 2D is a rear elevation view of the carrier shown in FIG. 2A;

FIG. 3A is a perspective view of the screw cartridge of the screw delivery system shown in FIG. 1A;

FIG. 3B is a top plan view of the screw cartridge shown in FIG. 3A;

FIG. 3C is a rear elevation view of the screw cartridge shown in FIG. 3A;

FIG. 3D is a side elevation view of the screw cartridge shown in FIG. 3A;

FIG. 3E is a sectional side elevation view of the screw cartridge shown in FIG. 3D taken along line 3E-3E;

FIG. 4A is a side elevation view of the driver of the screw delivery system shown in FIG. 1A;

FIG. 4B is a top plan view of the driver shown in FIG. 4A;

FIG. 5 is a sectional side elevation view of the screw delivery system illustrated in FIG. 1, showing the driver extending through both the carrier and a bore of the screw cartridge and mated with a screw that was disposed in the bore of the screw cartridge;

FIG. 6A is a side elevation view of the nose of the screw delivery system shown in FIG. 1A;

FIG. 6B is a front elevation view of the nose shown in FIG. 6A;

FIG. 6C is a sectional side elevation view of the nose shown in FIG. 6B taken along line 6C-6C;

FIG. 8A is a rear perspective view of a rotation assembly of the screw delivery system illustrated in FIG. 1, showing the nose disposed within the guide body, and the driver extending through a channel of the nose;

FIG. 8B is a side elevation view of the rotation assembly shown in FIG. 8A;

FIG. 13A is a schematic sectional side elevation view of a driver constructed in accordance with another embodiment, the driver having a driving portion that rotates as the driver is rotated by a user;

FIG. 13B is a schematic sectional side elevation view of a carrier configured to receive the driver shown in FIG. 13A;

FIG. 14 is a schematic sectional side elevation view of a driver constructed in accordance with another embodiment, the driver having an outer housing and a driving portion that rotates as the driving portion is received within the outer housing;

FIG. 17 is a schematic sectional side elevation view of a screw delivery system constructed in accordance with another embodiment, the screw delivery system including a plurality of pre-loaded drivers that are configured to rotate about a carrier such that each driver may be individually oriented to drive a pre-loaded fastener into tissue; and FIG. 18 is a schematic side sectional view of a screw delivery system constructed in accordance with another embodiment.

DETAILED DESCRIPTION

Figure 1A:
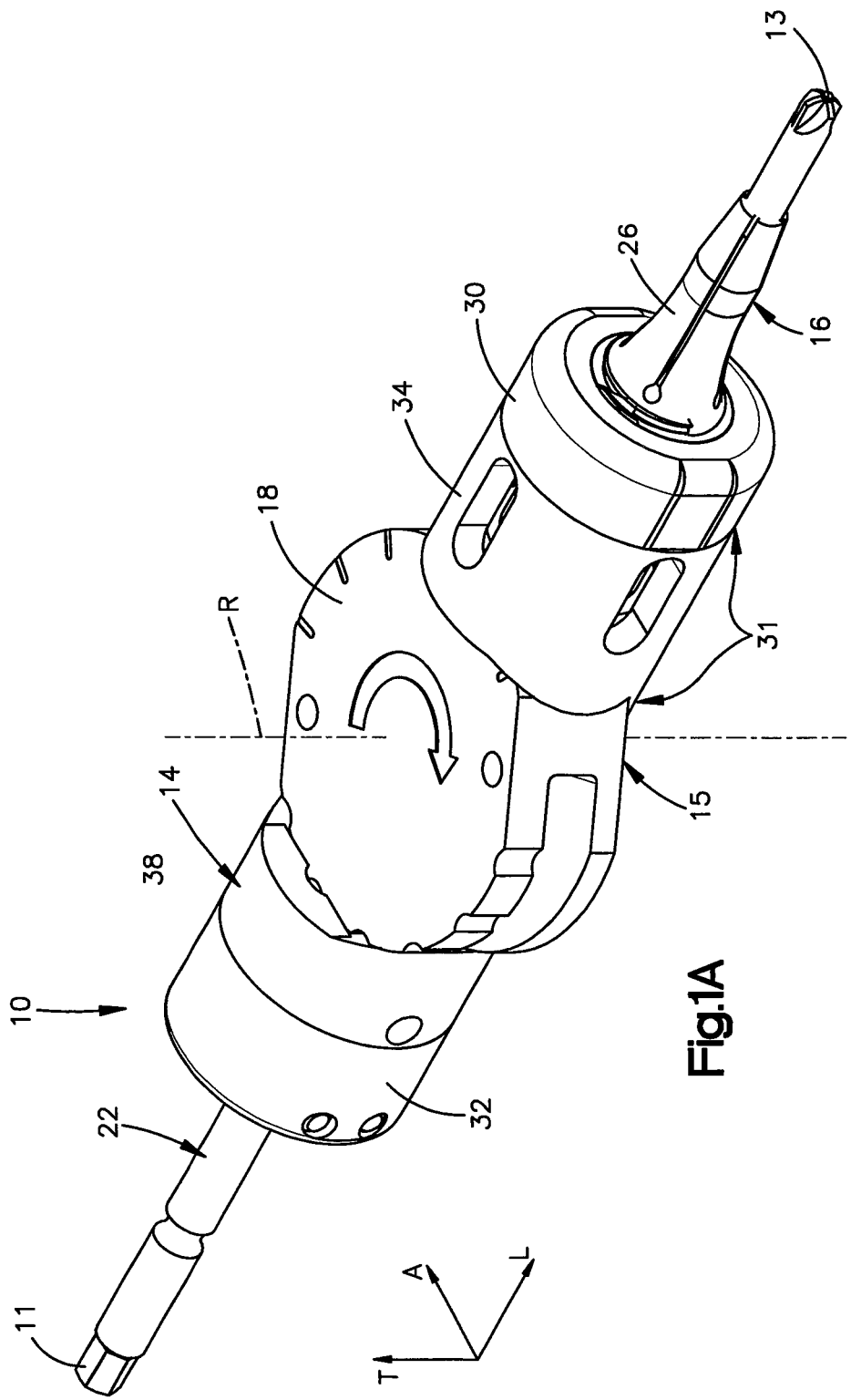
FIG. 1A is a perspective view of a screw delivery system constructed in accordance with one embodiment, the screw delivery system including a carrier that is configured to hold a screw cartridge, a guide body coupled to an end of the carrier, a driver that is disposed within the carrier, and a nose that is at least partially disposed within the guide body and rotates relative to the carrier as the driver is translated through the carrier.
Figure 1B:
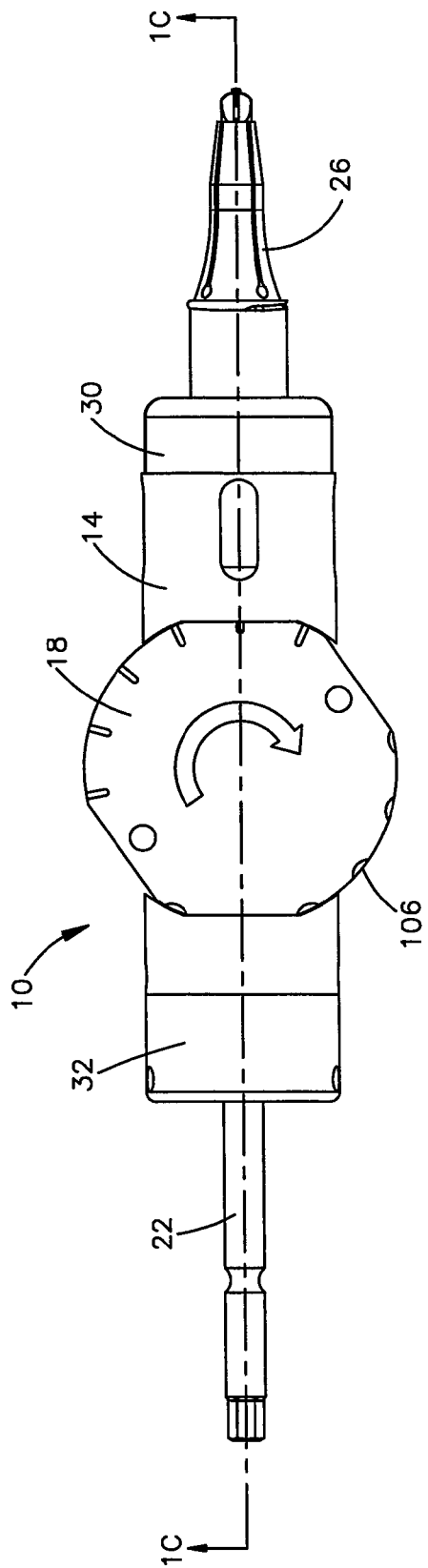
FIG. 1B is a top plan view of the screw delivery system shown in FIG. 1A.
Figure 1C:
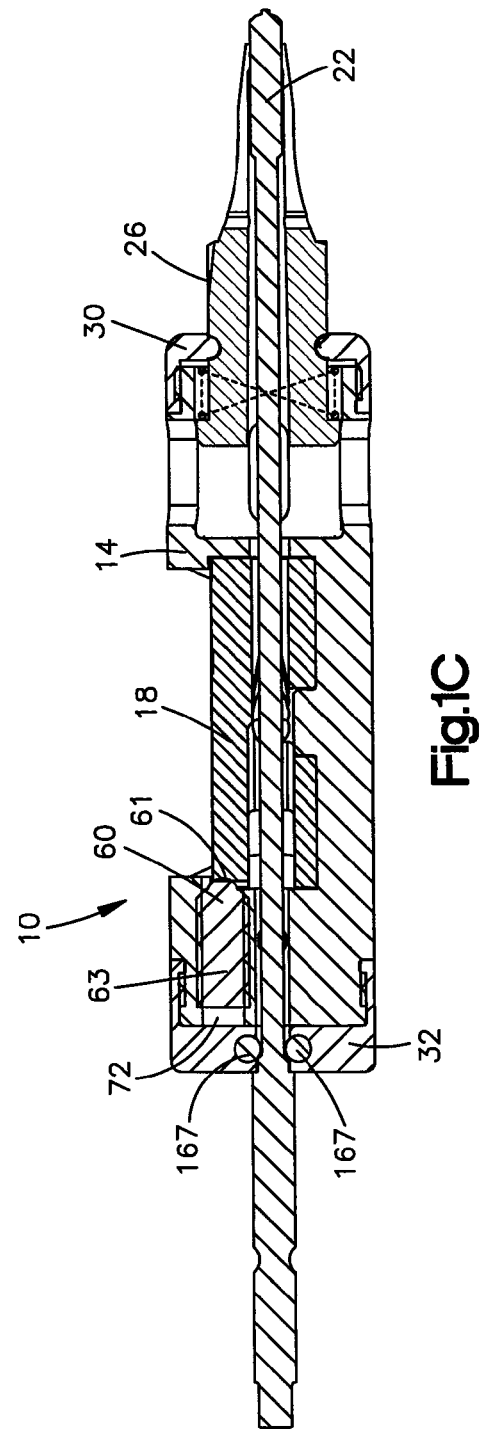
FIG. 1C is a sectional side elevation view of the screw delivery system shown in FIG. 1B taken along line 1C-1C.

Referring to FIGS. 1A-1C, a screw delivery system 10 is configured to automatically orient a driver to fasteners that are to be inserted into tissue. The screw delivery system 10 is configured to increase the delivery speed of fasteners to an implant site as well as predictably and repeatably place fasteners such as standard MatrixNEURO™ screws, commercially available from Synthes Inc. located in West Chester, Pa., onto a driver, with respect to conventional screw delivery systems. Such screws may be between about 1.5 mm and about 2 mm in diameter, and about 5 mm in length. Typically, up to between 6 and 50 screws can be used in a single fixation procedure. It should be understood, however, that the screw delivery system 10 is configured to deliver MatrixNEURO™ screws, or any suitable alternative screw.

Certain terminology may be used in the following description for convenience only and should not be considered as limiting in any way. For instance, the screw delivery system 10 is extending horizontally along a longitudinal direction "L" and further extending along a lateral direction "A" that extends substantially perpendicular to the longitudinal direction "L", and vertically along a transverse direction "T" that extends substantially perpendicular to both the longitudinal direction "L" and the lateral direction "A". The screw delivery system 10 is illustrated as elongated in the longitudinal direction L. Unless otherwise specified herein, the terms "lateral," "longitudinal," and "transverse" as used to describe the orthogonal directional components of the screw delivery system 10 are likewise used to describe the directional components of the remainder of the system 10. The screw delivery system 10 defines a longitudinal rear end 11 and a longitudinally front end 13, such that the directional terms "front" and "back" and derivatives thereof refer to a direction from the end 11 towards the end 13, and from the end 13 towards the end 11, respectively.

The terms "top," "bottom," "left," "right," "upper," and "lower" designate directions in the figures to which reference is made. Likewise, the terms "inwardly," "outwardly," "upwardly," and "downwardly" may designate directions toward and away from, respectively, the geometric center of the referenced object. The terminology includes the words above specifically mentioned, derivatives thereof, and words of similar import.

It should be appreciated that while the longitudinal and lateral directions "L" and "A" are illustrated as extending along a substantially horizontal plane, and that the transverse direction "T" is illustrated as extending along a substantially vertical plane, the planes that encompass the various directions may differ during use, depending, for instance, on the desired orientation of the delivery system 10 during use. Accordingly, the terms "vertical" and "horizontal" are used to describe the system 10 as illustrated merely for the purposes of clarity and convenience, it being appreciated that these orientations may change during use.

The screw delivery system 10 includes a carrier 14 that defines a front portion 34, a rear portion 38, and a receptacle 42 disposed between the front and rear portions 34 and 38. The system 10 further includes a fastener cartridge 18 disposed in the receptacle 42 of the carrier 14. The fastener cartridge 18 may be a screw cartridge that is rotatable relative to the front and rear portions 34 and 38 about a transverse axis of rotation R. As shown in FIG. 1A, the carrier 14 is configured to carry a guide body 30 that is disposed at a front end of the carrier 14, and a rear end cap 32 that is disposed at a rear end of the carrier 14. Disposed at least partially within the guide body 30 is a nose 26. The carrier 14 and the screw cartridge 18 may define a first upstream screw alignment assembly 15, while the nose 26 and guide body 30 may define a second downstream screw alignment assembly 16. It should be understood, however, that the carrier 14, screw cartridge 18, nose 26, and guide body 30 also together define a screw alignment assembly 31. The screw delivery system 10 further includes a driver 22 that extends longitudinally through both the first and second screw alignment assemblies 15 and 16. The screw delivery system 10 and in particular the driver 22 can be attached to a standard handle or a battery powered driver handle as desired.

Referring also to FIGS. 1A-1C, during operation, the driver 22 is initially pulled back out of interference with the receptacle 42, or removed from the alignment assembly 31 altogether. The screw cartridge 18 is then inserted into the screw cartridge receptacle 42 of the carrier 14, and rotated about the transverse axis R so that a first screw is aligned with the driver 22. In this regard, it should be appreciated that the receptacle 42 should be sized to securely receive and hold the cartridge 18, and at the same time allow rotation of cartridge 18 therein. The cartridge 18 is keyed to lock into place once turned so that the cartridge 18 does not unintentionally become removed from the receptacle 42 in the carrier 14.

The screw driver 22 is then translated forward through the cartridge 18 and the carrier 14 to thereby push a longitudinally aligned screw out of the cartridge 18 and into the nose 26. Translational forward movement of the screw driver 22 causes the head of the screw to become rotationally aligned with the tip of the driver 22 such that the tip of the driver engages the screw head. The nose 26 along with the screw are guided through the guide body 30 under a linear force applied by the driver 22 until the tip of the driver 22 and the head of the screw are aligned. Eventually, with continued linear force, the nose 26 separates, thereby allowing the driver 22 and screw to pass through for insertion into the implant site, for instance of underlying bone or other tissue or structure. Once completed, the driver 22 is retracted back through the nose 26, the cartridge 18 and the carrier 14. The cartridge 18 is then indexed to the next screw for implantation, and the process is repeated.

Referring to FIGS. 2A-2F, the carrier 14 includes a carrier body 44 that defines the front portion 34, the rear portion 38 and the receptacle 42 disposed between the front and rear portions 34, and 38. The carrier 14 is configured to securely support the cartridge 18 and the driver 22. The front portion 34 of the carrier body 44 defines a flange 46 that is configured to carry the guide body 30. The carrier 14 further includes a first longitudinal bore 54 that extends longitudinally through the carrier body 44 and is configured to receive the driver 22. The bore 54 generally extends through the center of the front portion 34 and the rear portion 38, and should be sized to allow the driver 22 to slide forward and rearward therein. It should be understood that the bore 54 may have varying diameters as it extends through the carrier body 44. For example, as the bore 54 extends through the front portion 34, the bore 54 may have a greater diameter than the portion of the bore 54 extending through the rear portion 38.

Figure 2E:
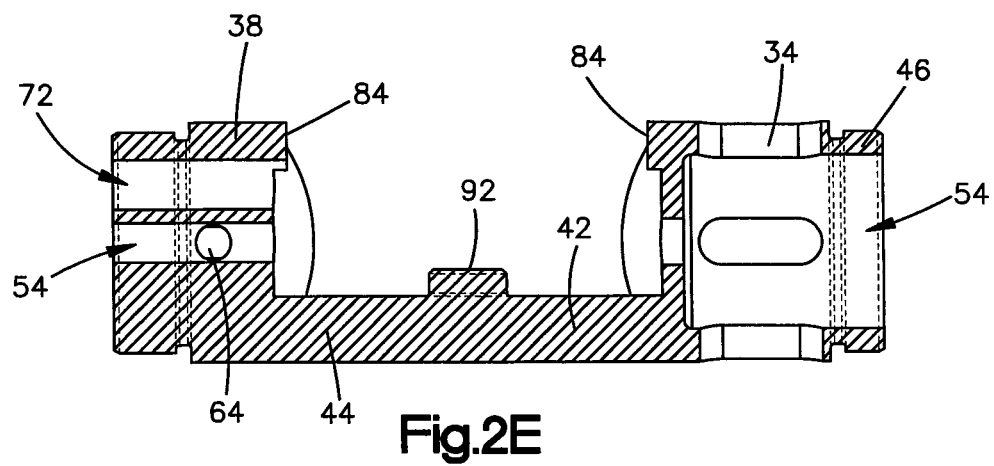
FIG. 2E is a sectional side elevation view of the carrier shown in FIG. 2B taken along line 2E-2E.
Figure 2F:
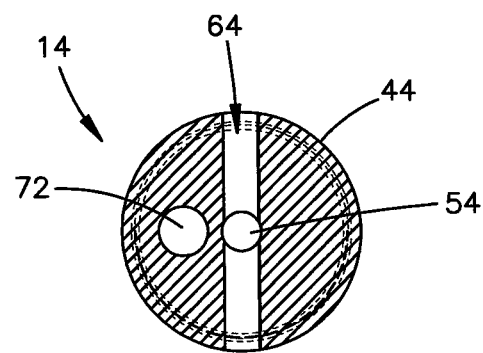
FIG. 2F is a sectional end elevation view of the carrier shown in FIG. 2B taken along line 2F-2F.

As shown in FIGS. 1C and 2D-2F the rear portion 38 defines a rear portion of the bore 54, and further includes a locking mechanism 60 disposed within a second longitudinal bore 72 that is located above the bore 54. As shown in FIGS. 2E and 2F, the rear portion 38 further defines a third lateral bore 64 that extends laterally through the carrier body 44. As shown in FIG. 2E, the second longitudinal bore 72 extends completely through the rear portion 38, and the third lateral bore 64 extends through the longitudinal bore 54. The third bore 64 is configured to contain a pair of ball detents 172 that are configured to engage the driver 22 to thereby center or otherwise hold the driver 22 within the carrier 14. The ball detents 172 also are configured to allow the driver 22 to translate more smoothly.

With continuing reference to FIGS. 1C and 2E, the locking mechanism 60 may include a ball bearing 61 and a spring 63 housed within the second bore 72. The spring 63 presses against the ball bearing 61 to bias the ball bearing forward. As the cartridge 18 is rotated within the receptacle 42, the ball bearing 61 will eventually engage detents 106 (see FIG. 3A) of the cartridge 18. In particular, during rotation of the cartridge 18, the ball bearing 61 is biased rearward until the cartridge 18 is in an aligned position (e.g., whereby a screw is aligned with the driver 22), at which point the ball bearing 61 will return forward to its original position under the force of the spring 63 and engage the detent 106, thereby locking the cartridge 18 in place. In this way, the locking mechanisms of the carrier and the cartridge may be considered an indexing system.

As shown in FIG. 2F, the third bore 64 extends laterally through the rear portion 38 of the carrier body 44. A ball detent is positioned in the third bore 64 and acts as a centering device for the driver 22. That is, when engaged, the ball detents center the driver 22 within the bore 54 of the carrier 14.

As shown in FIGS. 2A, 2B, and 2E, the receptacle 42 is defined between the front portion 34 and the rear portion 38 of the carrier body 44, such that the cartridge 18 can fit within the receptacle 42. As shown, both the front portion 34 and the rear portion 38 include an eve 84 that extends over a portion of the receptacle 42. A middle portion of a bottom 88 of the receptacle 42 includes a protrusion 92 for being received by a recess that extends into a bottom surface of the cartridge 18. The protrusion 92 is configured to keep the cartridge 18 centered within the receptacle 42.

Referring now to FIGS. 3A-3E, the cartridge 18 includes upper and lower plates 51 and 53 that each define curved front and rear surfaces 102 and 96, respectively, that are joined by opposing flat longitudinal side surfaces 110. The flat sides 110 help capture the cartridge 18 within the receptacle 42 of the carrier 14. For example, the cartridge 18 is placed in the receptacle 42 by aligning the cartridge flat sides 110 to the flats created by the eves 84 of the receptacle. The cartridge 18 is then dropped into the receptacle 42 such that the flat sides 110 are disposed below the eves 84. Once the cartridge 18 is in place in the receptacle 42, rotation of the cartridge 18 around axis R will allow the curved front 102 and rear surfaces 96 to be captured underneath the eves 84 of the receptacle 42 thereby preventing upward movement of the cartridge out of the receptacle 42. The cartridge 18 further includes a recess 94 that is disposed between the upper and lower plates 51 and 53. The recess 94 is open at the curved rear end 106, and open on both lateral sides as the recess extends forward from the rear surface 96 to a location rearward of the front curved surface 102. As illustrated, the recess 94 terminates at a location aligned with the side surfaces 110. The recess 94 is open at the rear surface 96. Thus, it should be appreciated that the driver 22 can extend into the recess 94 even as the recess is rotated about the axis R.

The cartridge 18 is configured to retain one or more fasteners, such as screws that are to be fastened to bone or other underlying structure. In particular, the cartridge 18 further includes a plurality of bores 98 that each extend inward from the curved front surface and terminate into the recess 94. In this way it may be said that the bores 98 extend from the front surface 102 and extend through to the rear surface 96. The cartridge 18 may be molded around the screws, thereby forming the bores 98. The cartridge 18 may be disposable and may contain several screws. The screws may be packaged loosely, so that they are contained without orientation to the driver 22. The screws can be oriented radially so that the screw delivery system 10 remains balanced over the center line and does not wobble as the carrier 14 is rotated. The cartridge 18 can include markings 77 corresponding to each screw retained therein, so as to allow a user to easily index the cartridge, either manually or automatically, to each screw position so that the screws can be quickly dispensed. Any remaining screws in the cartridge 18 may be removed easily from the cartridge 18 and placed in a sterilization module for later use. In practice, the screws may be provided sterile and the cartridge 18 may be disposed of once the screws are dispensed.

Each bore 98 of the cartridge 18 is adapted to securely hold a single screw, such as screw 116 illustrated in FIG. 3E. The bores 98 can be sized as desired, for instance having a diameter between 3 mm and 4 mm, such as a 3.3 mm diameter, and may contain screws of any desired length, such as 5 mm. In use, the driver 22 is translated forward through the recess 94 and through a first bore 98a to directly engage and retrieve a first screw 116. Once the first screw 116 is secured to bone, the driver can be retracted from the cartridge 18, such that the cartridge 18 can be rotated to place another one of the screws 116, for instance disposed in a second bore 98 that is adjacent the first bore 98a, in alignment with the driver 22. The driver 22 can once again be translated forward through the recess 94, and then through the second bore 98 to thereby directly engage and retrieve a second screw 116. This procedure can be continued as desired until all of the screws 116 are used.

As shown, the rear surface 96 of the cartridge 18 includes locking mechanisms, such as detents 106 that are in radial alignment with respective bores 98. The detents 106 are provided as vertically oriented rounded recesses extending into the rear surface 96. The locking mechanism 60 of the carrier 14 is adapted to engage each detent 106 as the cartridge 18 is rotated. Accordingly, when the locking mechanism 60 is engaged to detent 106a, for instance, the driver 22 will be aligned with the screw contained in the first bore 98a. Accordingly, the cartridge 18 and the carrier 14 allow the driver 22 to properly engage the respective bores 98 and screws retained therein. In this regard, the cartridge 18 and the carrier 14 can be said to provide the first alignment assembly 15.

When all of the screws of cartridge 18 are used, cartridge 18 may be removed from the receptacle 42 by aligning the flat surfaces 110 with the eves 84 and lifting the cartridge 18 vertically upward and out of the receptacle 42, and disposed. A second cartridge 18 may then be inserted within the receptacle 42 in the manner described above. This process may be completed as many times as necessary to complete the procedure. While the cartridge 18 is shown as having six screws, it should be understood that the cartridge 18 is not limited to six screws, and that any number of screws may be used.

Referring now to FIGS. 4A and 4B, the driver 22 includes a longitudinally elongate rod member 150, and a coupling 154 at the rear end of the rod 150, and a head portion 158 disposed at the front end of the rod member 150. The rod member 150 is substantially cylindrical in cross section. The coupling 154 may be any coupling capable of securely holding a handle, and can be adapted to receive a standard handle or battery powered handle. In the illustrated embodiment, the coupling 154 is a hex coupling adapted to fit into a hexagonal recess defined in a handle.

The head portion 158 is adapted to engage the head of a screw retained by the screw cartridge 18. As shown in FIG. 4A, the head portion 158 defines a mating feature adapted to mate with a corresponding mating feature of the screw. As illustrated, the head portion 158 defines a cruciform 159 that is adapted to engage a cruciform defined by the head of a screw. As shown in FIGS. 4A and 4B, the rod member 150 also includes a pair of front stops 162, a pair of rear stops 166, and a pair of recesses 170 defined between the front and rear stops. As shown, front stops 162 are proximate to the head portion 158, while the rear stops 166 are proximate to the coupling 154. Referring back to FIG. 1C, the front and rear stops 162 and 166 are each positioned to come into contact with pins or bolts 167 that extend within the rear end cap 32. Thus, when the driver 22 is pulled fully back, the pins 167 will contact the rear edges of the front stops 162 and when the driver 22 is fully forward, the pins 167 will contact the front edges of the rear stops 166. The recesses 170 should provide enough clearance so that the pins 167 do not interfere with the driver 22 as the driver 22 is being slid forward or rearward between its fully forward and fully rearward positions. Furthermore, the pins 167 extend within the rear end cap 32 such that they are positioned within the recesses 170 (i.e. below and above the rod member 150) to thereby prevent the driver 22 from rotating as it is translated forward and rearward.

As shown in FIG. 5, the driver 22 may be translated through the bore 54 of the carrier 14 and through a bore 98 of the cartridge 18. Once the driver 22 has picked up a fastener from the cartridge 18, the driver 22 may push the fastener through the downstream alignment assembly to thereby align the head of the fastener with the head of the driver. Further advancement of the driver 22 will mate the driver 22 with the fastener. The driver 22 may then by rotated to drive the fastener into the underlying structure.

A handle may be attached to the coupling 154 of the driver 22. The handle may include a first portion separated from a second portion by a washer. The first portion preferably should be ergonomically shaped so that a user may comfortably hold the handle. The first portion may be independent from second portion which may be attached to the driver, and may be capable of rotating independent of the driver. Thus, if the driver rotates while picking up a screw, the first portion can remain stationary within a user's hand. Once the driver 22 picks up a screw, however, the user may grab the second portion and rotate it to thereby rotate the driver and securely place the screw into the bone.

Referring now to FIGS. 6A-6C, 7A-7C, and 8A-8C, the nose 26 is configured to receive, and hold a screw while the head portion 158 of the driver 22 is being aligned to the mating feature of the screw head. Mating of the driver 22 with a screw is accomplished by moving the nose 26 through the guide body 30. This will cause the screw and the nose 26 to turn a specified amount to align the head portion 158 of the driver 22 to the screw head, such that the head portion 158 can mate with the mating feature of the screw head. Once the nose 26 stops and can no longer be guided through the guide body 30, with continued linear force, the nose 26 separates to allow the screw and driver 22 to pass through and out of the nose 26. The nose 26 will separate by application of a sufficient force to allow the screw to be wedged onto the head portion 158 of the driver 22. Though not required, it is preferable that the nose 26 is made from titanium.

As shown in FIGS. 6A-6C, the nose 26 includes a nose body 209 that can be generally shaped as a cone or a frustum. In particular, the nose body 209 includes a rear portion 210 integrally connected to a front portion 212. The rear portion 210 is curved and defines a concave outer surface 214 having an outer diameter greater at the rear end than at the front end. The front portion 212 is beveled inwardly along a longitudinally forward direction. A plurality of slits 218 extend longitudinally into the front portion 212 and extends rearward into the rear portion 210 so as to divide the body 209 into a plurality of substantially identical flexible fingers 222. As shown in FIG. 6C, the body 209 and thus fingers 222 define an internal channel 225. As shown, the internal channel 225 includes a substantially cylindrical surface 226 that extends the length of the channel 225. Proximate to a front end of the channel 225, the surface 226 begins to angle radially inward to define an angled surface 228. The angled surface 228 terminates at an opening 230 of the body 209.

The internal channel 225 is sized to allow a screw from the cartridge 18 to pass through. As the screw is pushed through the channel 225, the fingers 222 begin to flex or otherwise spread and once the screw shaft or head contacts the angled surface 228 or the opening 230 of the body 209, additional force is required to spread the fingers 222 even further to allow the driver 22 and the screw to be pushed out of the nose 26. The additional force (at least 1.5 lbs of force) allows the screw to be wedged onto the head portion 158 of the driver 22. Preferably the angled surface 228 defines a 30 degree angle to create a force capable of sufficiently wedging the screw onto the driver 22, while making it easy enough to push the screw out of the nose 26.

As shown in FIG. 6C, the opening 230 should be smaller than the outer diameter of the screw threads so that the screw is rigidly held as the nose 26 moves through the guide body 30. For example, the opening 230 may have a diameter of 1.4 mm while the screw thread may have a major diameter of 1.5 mm. The smaller opening 230 thus captures the screw so that it turns with the nose 26 as it moves through the guide body 30.

The outer surface 214 of the rear portion 210 is curved to spread stress along the length of the rear portion 210. This ensures that stress levels do not exceed fatigue or yield stress during separation. A stress point at the base of the nose body 209 may also be eliminated by providing a bulge 233 that extends radially inward from the internal surface 226 of the channel 225.

The nose 26 further includes a shaft 234 that extends rearward from the nose body 209. As shown, the shaft 234 is cylindrical and includes a flange 236 at its rear end. The flange 236 is adapted to compress a spring against a stop defined by the guide body 30 as the nose 26 is advanced through the guide body 30. Once the screw has been placed and the driver 22 reversed, the spring will force the nose 26 back to its original position. The shaft 234 also includes or otherwise carries at least a first guide member 238. In the illustrated embodiment, the first guide member 238 is a helical groove 239 that extends along the shaft 234. The helical groove 239 is configured to be engaged by a guide member that is carried by the guide body 30 such that as the nose 26 is advanced through the guide body 30 the nose 26 rotates with respect to the guide body 30.

Figures 7A, 7B:
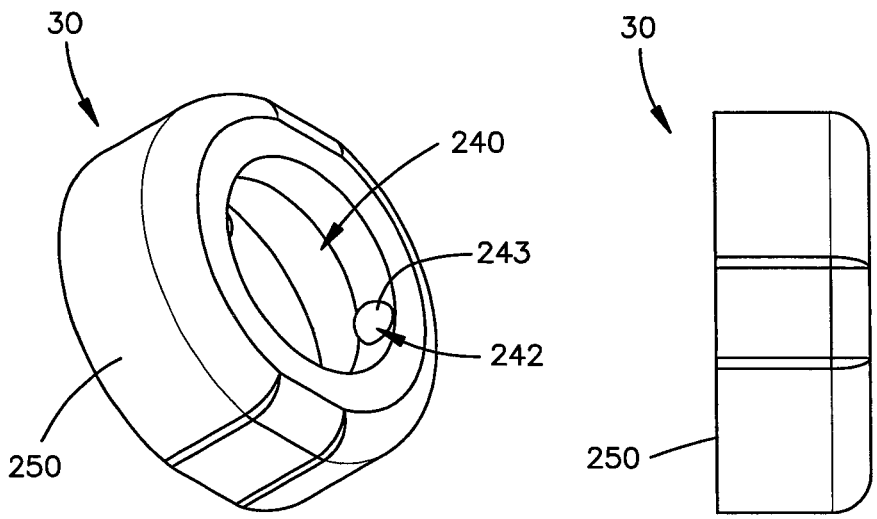
FIG. 7A is a perspective view of the guide body of the screw delivery system shown in FIG. 1A.
FIG. 7B is a top plan view of the guide body shown in FIG. 7A.
Figure 7C:
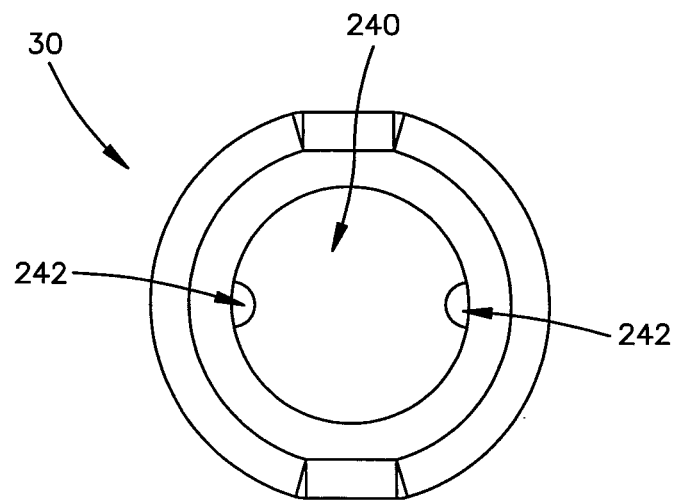
FIG. 7C is a front elevation view of the guide body shown in FIG. 7A.

Referring now to FIGS. 7A-7C, the guide body 30 is configured to be carried by the carrier body 44. In the illustrated embodiment, the guide body 30 is configured to be removably attached to the carrier body 44. As shown, the guide body 30 is generally cylindrical or conical in shape. As shown, the guide body 30 includes a bore 240 that extends completely therethrough. The guide body 30 further includes at least one guide member 242 that is configured to engage the guide member 238 defined by the nose 26. In the illustrated embodiment, the guide member 242 is a pair of opposing protrusions 243 that extend radially inward from an internal surface 244 of the bore 240.

The guide body 30 also includes a coupling flange 250 that extends rearward and is configured to interfaces with the flange 46 of the carrier 14. For example the flange 250 may include threads that engage threads formed on the flange 46. Though it should be understood that the guide body 30 and the carrier 14 may be made as one piece, may be welded together, or may be secured together using an interference fit.

The guide body 30 preferably is made from a metal material. Though it should be understood that the guide body 30 may be made from any material that allows the nose 26 to rotate within it. Accordingly, the guide body 30 may also be made from a hard plastic material.

Figure 8C:
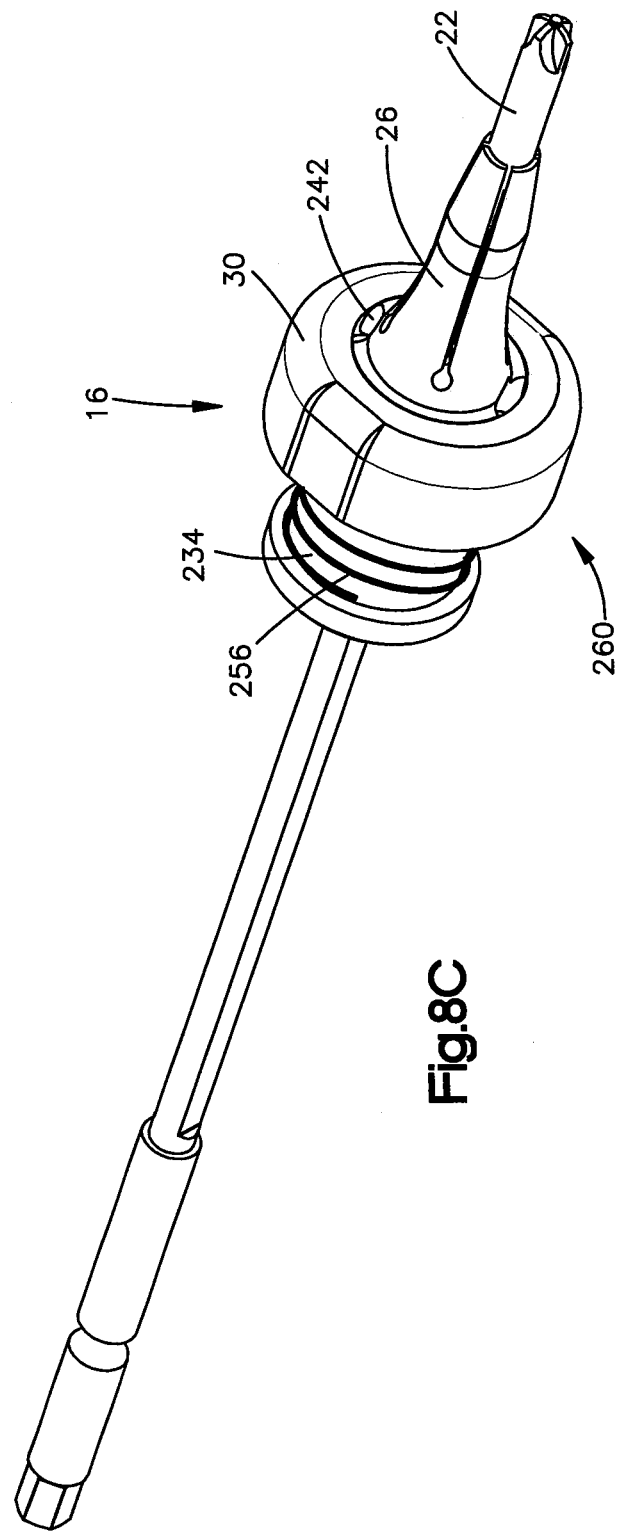
FIG. 8C is a front perspective view of the rotation assembly shown in FIG. 8A.

In operation and in reference to FIGS. 8A-8C, the guide body 30 allows the nose 26 to rotate as it travels through the guide body 30. That is, the protrusions 243 of the guide body 30 engage the helical grooves 239 of the nose 26 and causes the nose 26 to rotate as it travels through the guide body 30. The helical grooves 239 allow the nose 26 to rotate enough to allow the head of the driver 22 to mate with the mating feature defined by the head of a screw. For example, the helical grooves 239 may be designed to allow the nose 26 to rotate 90 degrees for mating features that define a cruciform. It may be preferred, however, to have grooves 239 be designed to rotate the nose 26 135 degrees in a specified distance to ensure sufficient rotation for mating features that define a cruciform. For example, it may be preferred to have the nose 26 rotate 135 degrees in about 9 mm of longitudinal forward travel. It should be understood, however, that rotation angles may very depending on the mating features (cruciform, flat, hexagonal, etc.) used. As shown in FIGS. 8A and 8B, there is a spring 256 between the guide body 30 and the flange 236 of the nose 26. The spring 256 controls the motion of the nose 26 and once the spring 256 is in a collapsed position, it acts as the stop for the nose 26. Thus, once the nose 26 travels a specified distance, the spring 256 will become fully compressed. At this point, the nose 26 stops, while the driver 22 with a screw continue to travel and exit the nose 26 and guide body 30. After the screw has been inserted into bone, the driver 22 can be retracted and the spring 256 will force the nose 26 back to its original position. Therefore, as this process is repeated, the nose 26 will always start from the same position.

The rotational relationship between the nose 26 and the guide body 30 defines a rotation assembly 260 that enables the nose 26 which holds the screw to rotate relative to the guide body 30 thereby rotating the screw relative to the driver 22. It should be understood, however, that the rotation assembly 260 may be any mechanism that enables relative motion between the driver 22 and a screw. Thus, a rotation assembly 260 also includes mechanisms that enable the driver head to rotate relative to the screw as the driver is translated forward.

FIGS. 8A-8C also show the interaction between the driver 22, the nose 26, and the guide body 30. As shown, as the driver 22 is pushed forward, the nose 26 is capable of advancing forward within the guide body 30. In particular, as the driver 22 picks up a screw from the cartridge 18, the screw will advance into the nose 26 and contact the opening 230 of the nose 26. When the screw contacts the nose opening 230, the interference between the screw and the nose opening 230 will cause the nose to advance forward with the screw. At this point, the protrusions 243 of the guide body 30 engage the helical grooves 239 of the nose 26 to thereby cause the nose 26 along with the screw to rotate about the longitudinal axis L as the nose 26 is advanced in the forward direction. As the nose 26 and the screw rotate, eventually the head of the driver 22 will be aligned with and mate with the head of the screw. In this regard, the nose 26 and the guide body 30 can be said to provide the second alignment assembly 16.

Figure 9A:
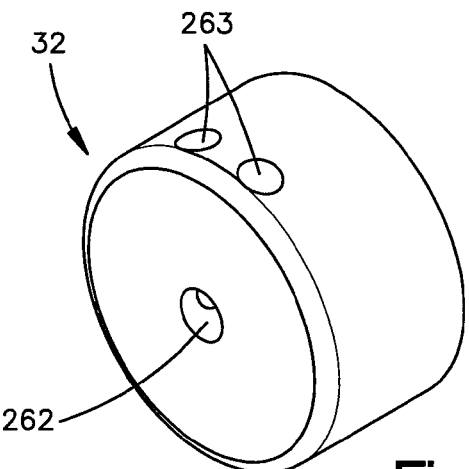
FIG. 9A is a rear perspective view of a rear cap that is configured to attach to a rear end of the carrier body.
Figure 9B:
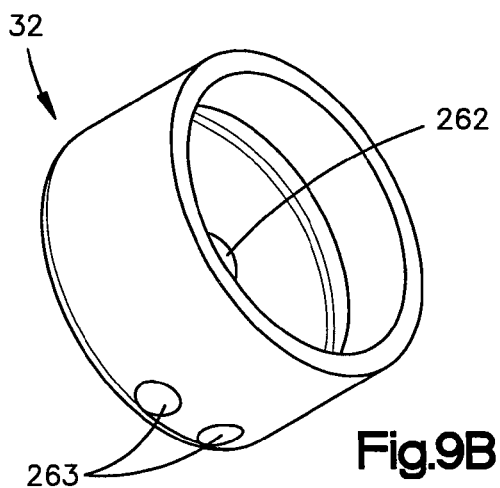
FIG. 9B is a front perspective view of the rear cap shown in FIG. 9A.
Figure 9C:
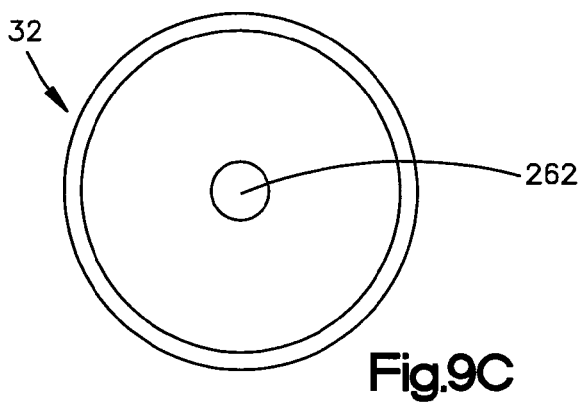
FIG. 9C is a rear elevation view of the rear cap shown in FIG. 9A.

As shown in FIGS. 9A-9C, the system 10 may also include a rear end cap 32 that is configured to be removably coupled to a rear end of the carrier body 44. As shown, the rear cap 32 defines a longitudinal bore 262 extending therethrough and a pair of lateral bores 263 that extend therein. The longitudinal bore 262 is configured to receive the driver 22 and the lateral bores 263 are configured to receive the pins 167 that prevent the driver 22 from rotating. The pins 167 also are configured to limit the forward and rearward travel of the driver 22 with respect to the carrier 14.

Figure 10A:
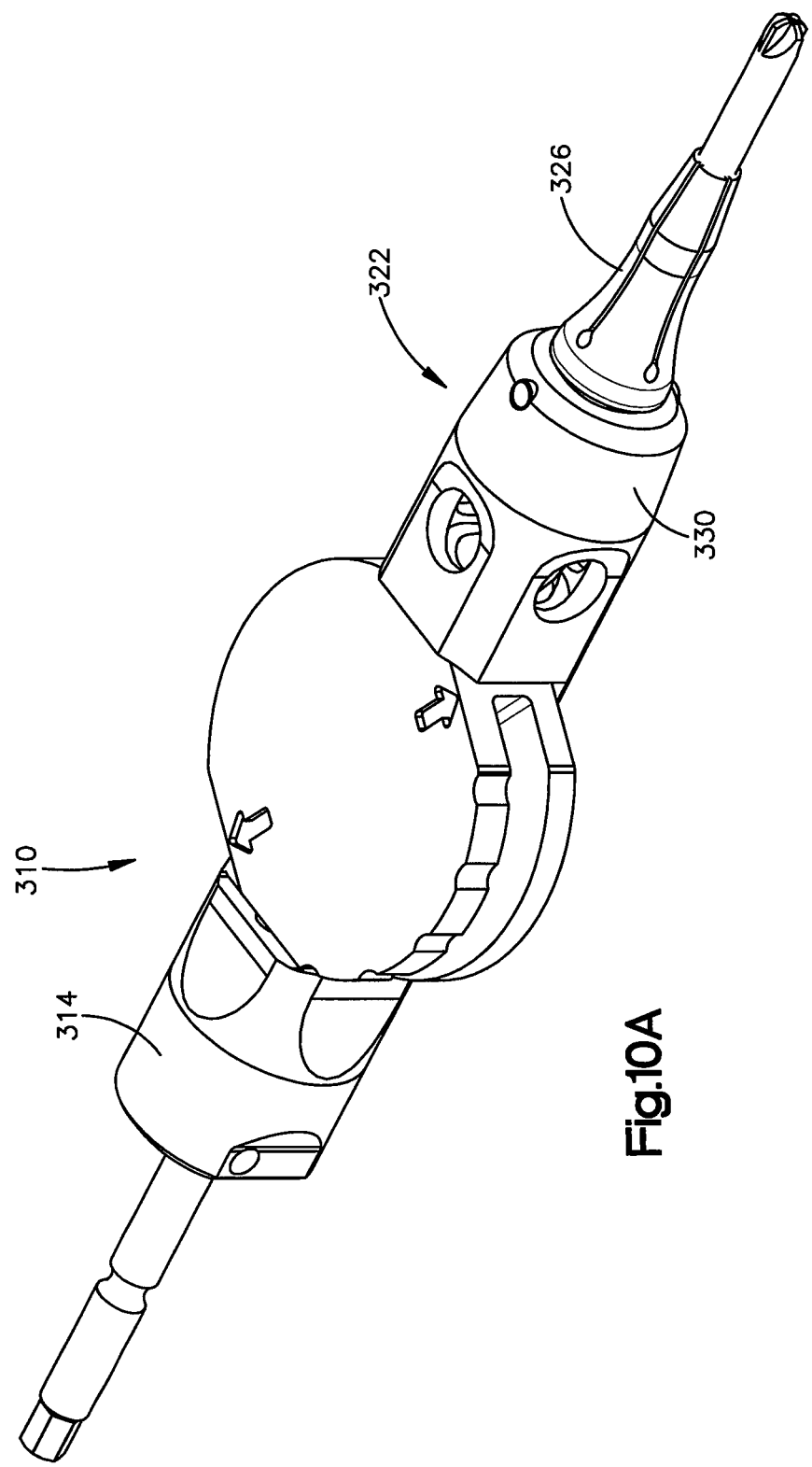
FIG. 10A is a perspective view of a screw delivery system constructed in accordance with another embodiment, the screw delivery system including a carrier body, and an alignment assembly that includes a nose and a guide body configured to be decoupled from the carrier body as a single unit.
Figure 10B:
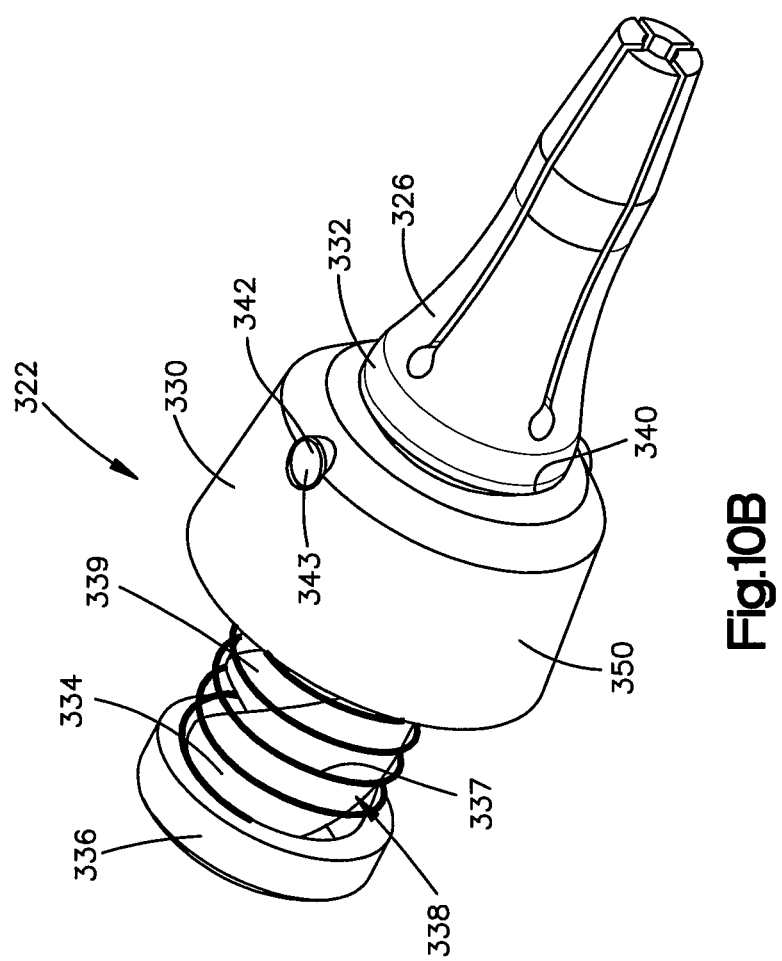
FIG. 10B is a perspective view of the alignment assembly shown in FIG. 10A.

In reference to FIGS. 10A-10B the screw delivery system may include a nose and guide body that form an alignment assembly configured to be decoupled from the carrier body as a single unit. As shown, a screw delivery system 310 include a carrier 314 and a downstream screw alignment assembly 322 removably attached to front end of the carrier 314. As shown, the alignment assembly 322 includes a nose 326 that is rotatably coupled to a guide body 330. The nose 326 and the guide body 330 form a single unitary unit that may be removably coupled to the carrier 314.

As shown in FIG. 10B, the nose 326 includes a nose body 332 that is similar to the nose body shown in FIGS. 6A-6C, and a shaft 334 that extends rearward from the nose body 332. As shown, the shaft 334 is cylindrical and includes a flange 336 at its rear end. The flange 336 is adapted to compress a spring 337 against a stop defined by the guide body 330 as the nose 326 is advanced through the guide body 330. Once the screw has been placed and the driver 22 reversed, the spring 337 will force the nose 326 back to its original position. The shaft 334 also includes or otherwise carries at least a first guide member 338. In the illustrated embodiment, the first guide member 337 is a helical groove 339 that extends along the shaft 334. The helical groove 339 is configured to be engaged by a guide member that is carried by the guide body 330 such that as the nose 326 is advanced through the guide body 330 the nose 326 rotates with respect to the guide body 330.

The guide body 330 includes a bore 340 that extends completely therethrough. and at least one guide member 342 that is configured to engage the guide member 338 defined by the nose 326. In the illustrated embodiment, the guide member 342 is a pair of opposing protrusions 443 that extend radially inward from an internal surface of the bore 340. The guide body 330 also includes a coupling flange 350 that extends rearward and is configured to interfaces with the carrier 314. Preferably the flange 350 includes threads that are opposite to the helical groove 339 defined by the nose 326. Therefore if the helical groove winds clockwise about the shaft 334, the threads of the flange 350 would be counterclockwise. In the illustrated embodiment, when the guide body 330 is decoupled from the carrier 314 the guide body 330, and nose 326 may be removed as a single unitary unit.

Figure 11A:
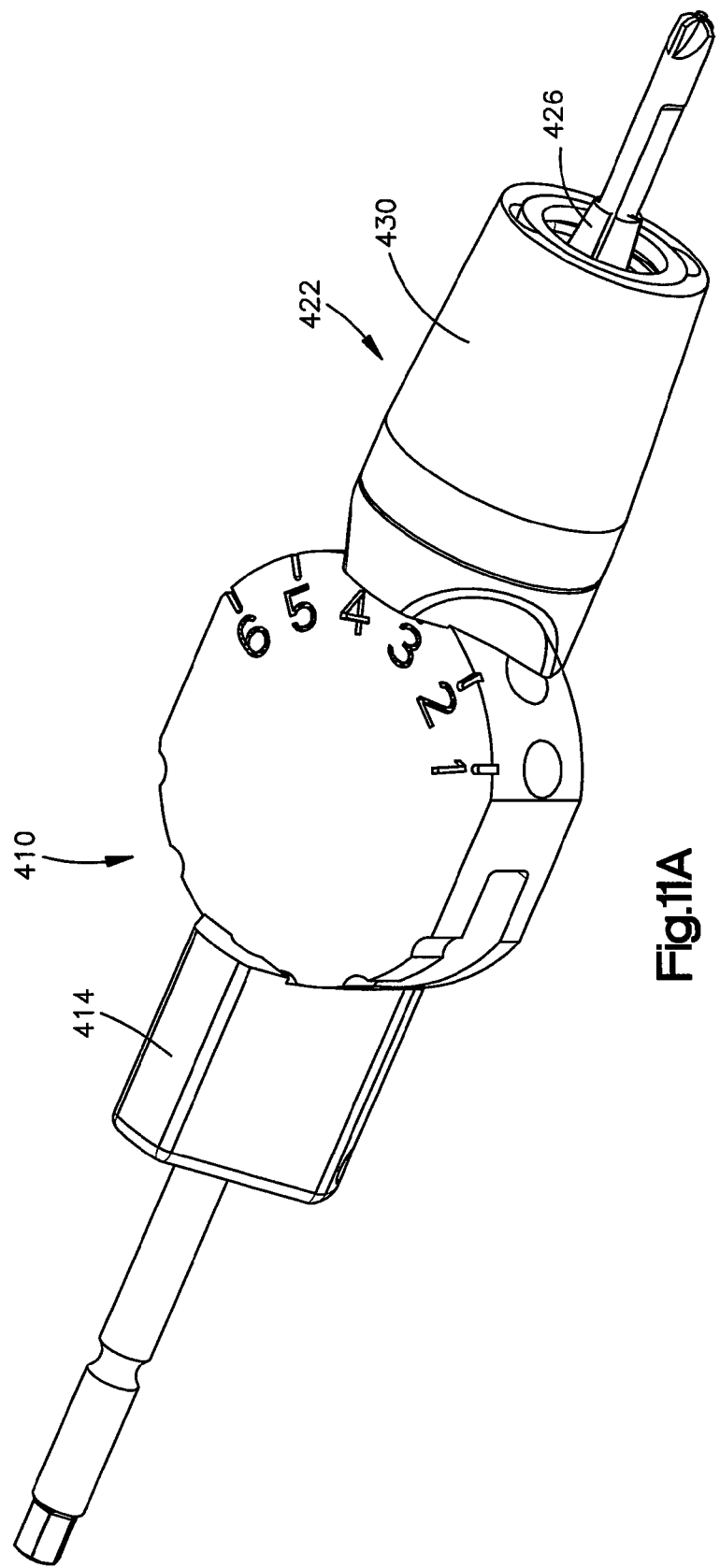
FIG. 11A is a perspective view of a screw delivery system constructed in accordance with another embodiment, including a nose that defines at least one protrusion and a guide body that defines at least one helical groove.

In reference to FIGS. 11A-11E, the screw delivery system may include a nose and guide body having alternative engagement members for allowing the nose to rotate as it is advanced through the guide body. As shown in FIG. 11A, a screw delivery system 410 includes a carrier 414 and a downstream screw alignment assembly 422 removably attached to a front end of the carrier 414. As shown, the alignment assembly 422 includes a nose 426 that is rotatable within a guide body 430.

Figure 11B:
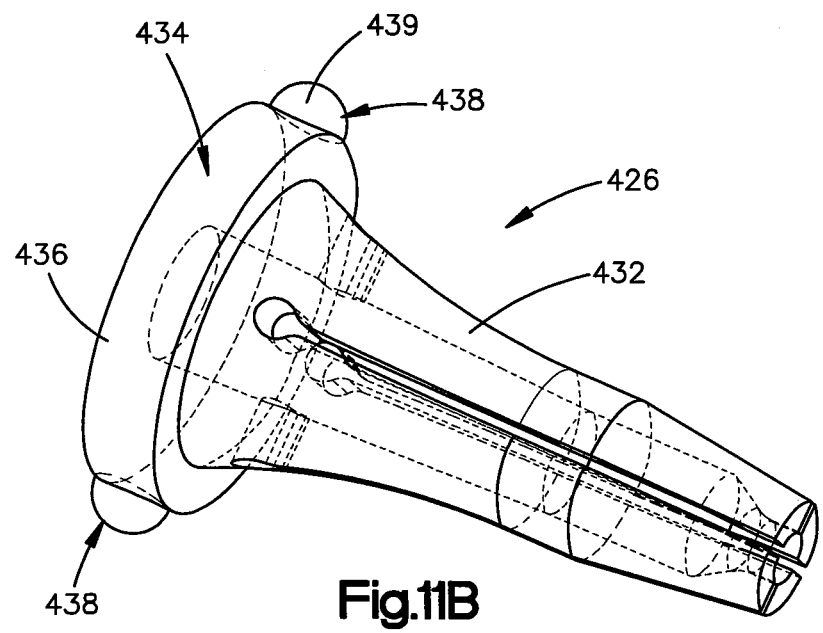
FIG. 11B is a perspective view of the nose shown in FIG. 11A, wherein the nose defines an internal channel shown in phantom lines.
Figure 11C:
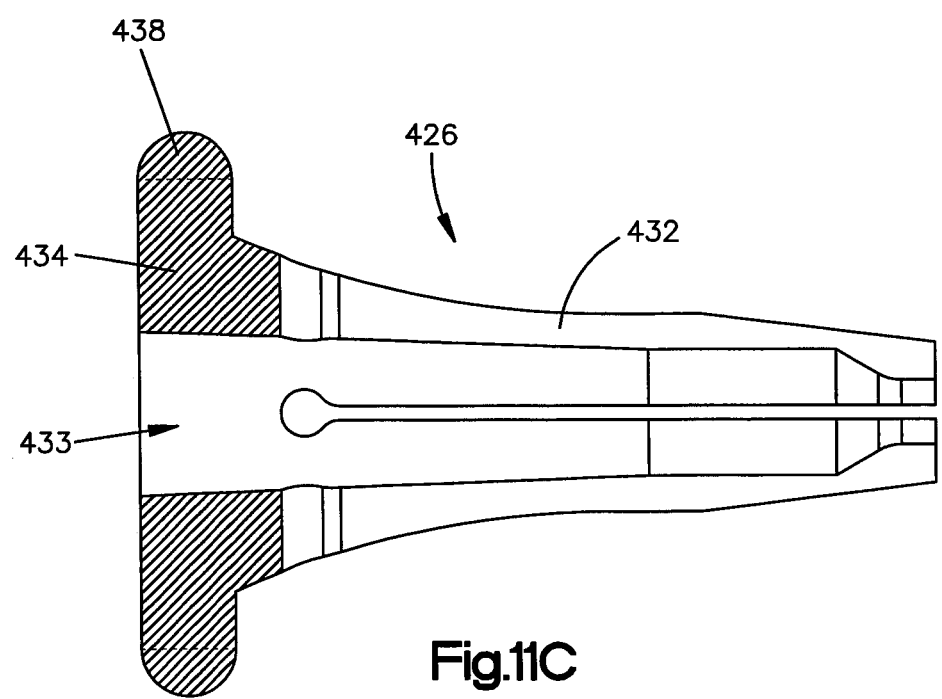
FIG. 11C is a sectional side elevation view of the nose shown in FIG. 11B.

As best shown in FIGS. 11B and 11C, the nose 426 includes a nose body 432 that is similar to the nose body shown in FIGS. 6A-6C, and a shaft 434 that extends rearward from the nose body 432. As shown in FIG. 11C, the nose body 432 defines a channel 433 that extends longitudinally through the body 432. The channel 433 is configured to receive a fastener such as a screw. As shown in FIG. 11B, the shaft 434 is cylindrical and defines a flange 436 that carries at least a first guide member 438. In the illustrated embodiment, the guide member 438 is a pair of protrusions 439 that extend radially out from the flange 436. The protrusions 439 are configured to engage a guide member that is carried by the guide body 430 such that as the nose 426 is advanced through the guide body 430 the nose 426 rotates with respect to the guide body 430.

Figure 11D:
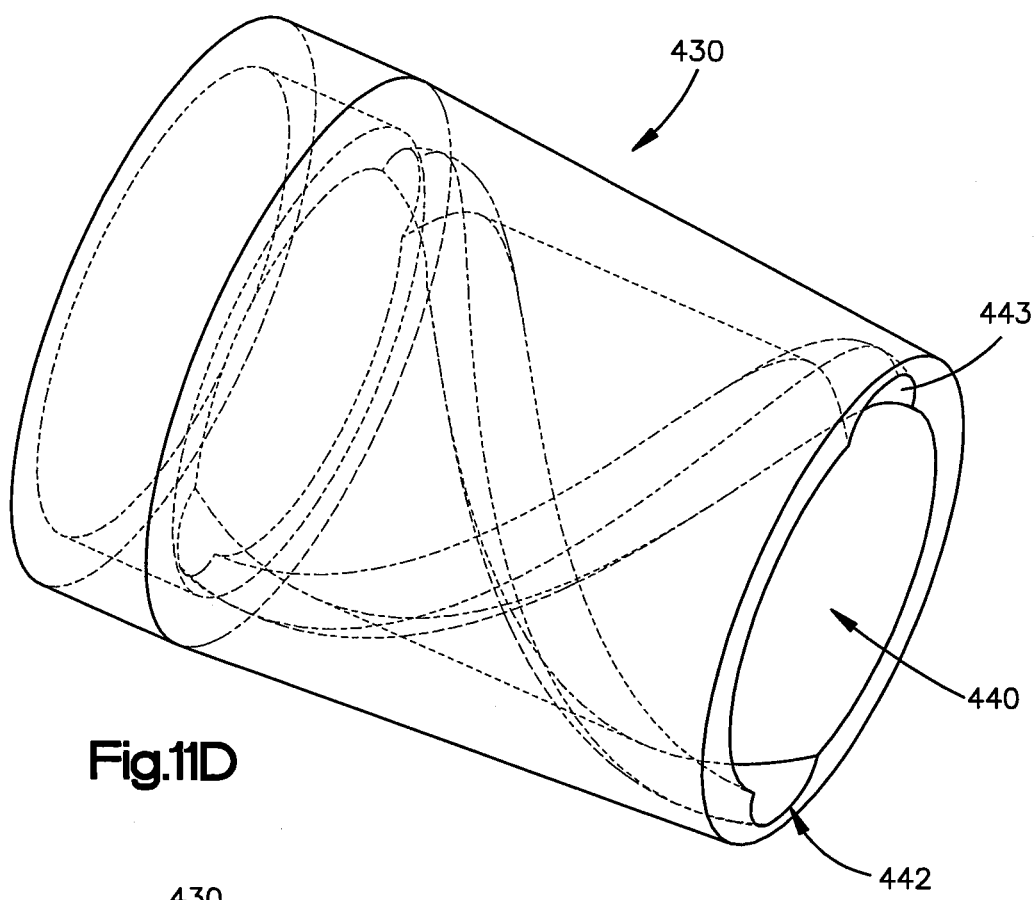
FIG. 11D is a perspective view of the guide body shown in FIG. 11A, wherein the guide body defines internal helical grooves shown in phantom lines.
Figure 11E:
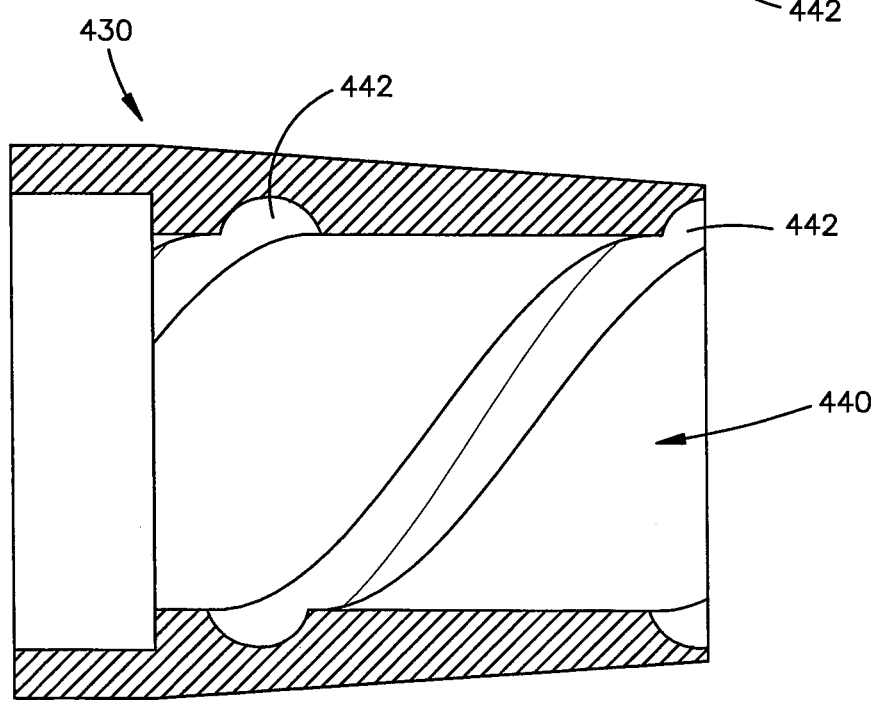
FIG. 11E is a sectional side elevation view of the guide body shown in FIG. 11D.

As shown in FIGS. 11D and 11E, the guide body 430 includes a bore 440 that extends completely therethrough and at least one guide member 442 that is formed on an interior surface of the bore 440. In the illustrated embodiment, the guide member 442 is a pair of helical grooves 443 that are configured to be engaged by the protrusions 439 carried by the nose 426. Therefore, as the nose 426 is advanced through the guide body 430, the nose 426 will rotate a specified amount that is determined by the length of the helical grooves 443 of the guide body 430.

Figure 12:
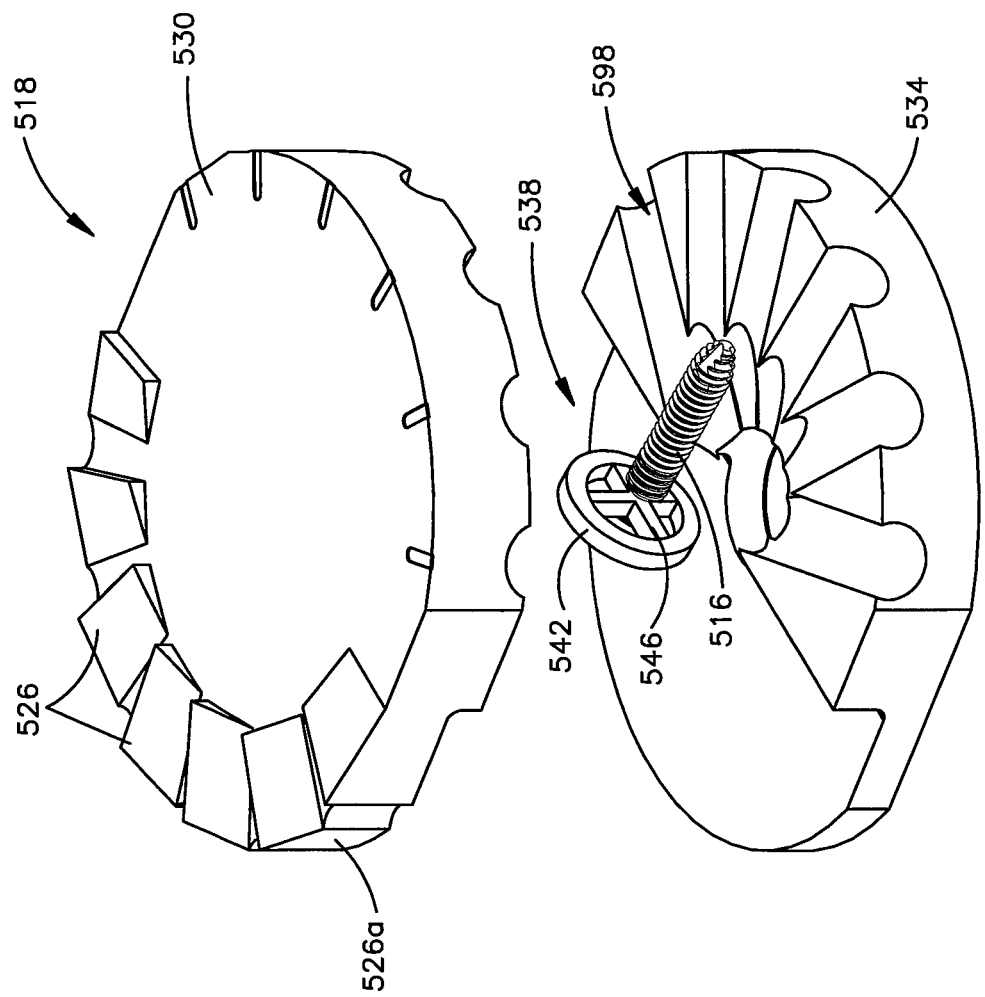
FIG. 12 is an exploded perspective view of a screw cartridge constructed in accordance with another embodiment, the screw cartridge defining a locking mechanism that is configured to be engaged by a ratchet.

Now in reference to FIG. 12, it should be understood that the screw delivery system may include suitable alternative cartridges. For example, as shown in FIG. 12, a cartridge 518 includes a top plate 530 vertically spaced from a bottom plate 534. The top plate 530 and the bottom plate 534 may be selectively separable to install or remove screws from the bores of the cartridge 518. The cartridge 518 further includes teeth 526, as opposed to detents 106 of the cartridge 18. The teeth 526 extend up at an angle from the top plate 530. As shown, each tooth 526 includes an angled surface that extends counterclockwise about the transverse axis, and a substantially vertical surface that extends down from an end of the angled surface. Accordingly, the locking mechanism of the carrier such as carrier 14, can be provided as a ratchet that engages the teeth 526. For example, the locking mechanism may include a longitudinal arm having a head at its distal end. The longitudinal arm along with its head will be capable of flexing upward. As the cartridge 518 is rotated counterclockwise, the head of the ratchet will ride along the angled surface of a first tooth 526a, and flex upward. Once the head goes beyond the angled surface it will return to its original position and abut the vertical surface of the tooth thereby locking the cartridge 518 in place.

The cartridge can include a plurality of bores 598 in the manner described above with respect to bores 98 of cartridge 18, however the cartridge 118 can further include a screw capture device 538 disposed into each bore 598, to securely hold the screws 516 within the cartridge 518. As shown, the screw capture device 538 is a ring 542 having spokes 546 extending around the screw. An outer surface of the ring 542 will abut an inner surface of a respective bore 598. Preferably there will be an interference fit between the outer surface of the ring 542 and the inner surface of the bore 598. When the driver 22 pushes forward against the screw 516, the lateral force will cause the spokes 546 to deflect to thereby disengage the screw 516 from the screw capture device 538 and allow the screw 516 to pass through the bore 598. It should be understood that the features of the cartridge 518 may be incorporated into the cartridge 18, and vice versa. For example, the cartridge 18 may also include a screw capture device.

Now in reference to FIGS. 13A-13B and 14, while the embodiments described above include features that mates the screw with a driver by rotating the screw to match the driver mating end, it should be understood that it is envisioned that the driver could be rotated.

In reference to FIGS. 13A and 13B, a screw delivery system may include a driver 622 that rotates within a carrier 626. As shown, the driver 622 includes a driving portion 630, and an outer housing 634. The outer housing 634 includes threads 638 that mate with internal threads 642 of the sleeve 626. As the driver 622 is advanced forward, it rotates due to the threaded relationship between the driver 622 and the sleeve 626. The rotation of the driver 622 allows it to locate and mate with the head of a screw without requiring the user to provide a rotating motion. In this way, the driver 622 defines a rotation assembly 260. As shown in FIG. 13A, the outer housing 634 of the driver 622 includes an internal spring 646 that allows the driving portion 630 to contract instead of pushing the screw through a screw capture device while the driver 622 is locating the screw. Thus, the screw delivery system provides relative rotation between a screw to be inserted and the screw driver so as to allow the mating features of the screw and the driver to register and mate before the screw exits the screw delivery system.

In another embodiment and in reference to FIG. 14, the screw delivery system may include a different driver 722 that is configured to rotate to mate with the head of a screw. Like the driver 622, as a user advances the driver 722 linearly, the driver 722 rotates without requiring the user to provide a rotating motion. As shown, the driver 722 includes a driving portion 726 and an outer housing 730. As the outer housing 730 collapses onto the driving portion 726, the driving portion 726 will rotate. This is because the driving portion 726 includes a mating member such as a pin 734, and the outer housing 730 includes mating member such as a helical track 738 that mates with the pin 734 of the driving portion 726. In this way the driver 722 defines a rotation assembly 260. A spring 742 is located within the outer housing 730 and is configured to force the driving portion 726 forward.

Figure 15:
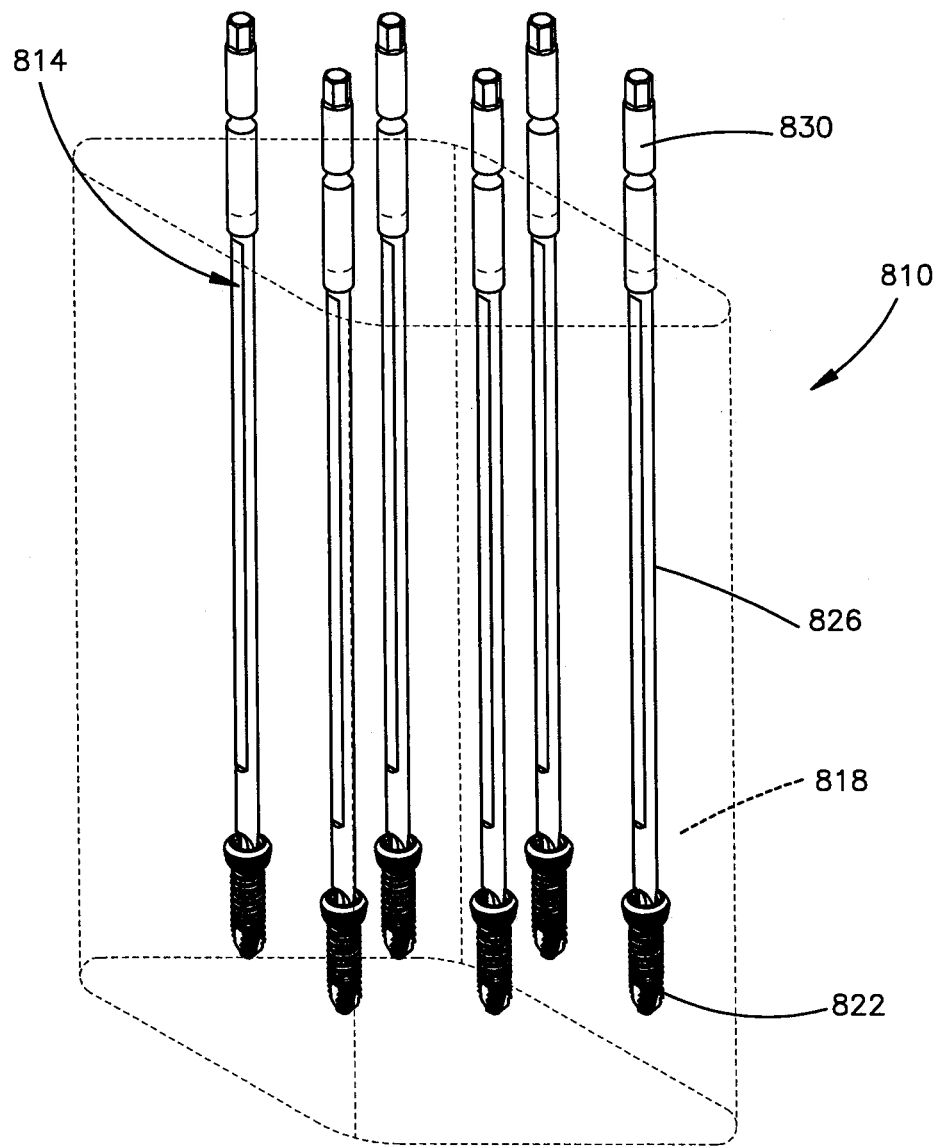
FIG. 15 is a perspective view of a screw delivery system in accordance with another embodiment, the screw delivery system including a plurality of pre-loaded drivers disposed within a carrier.

In reference to FIG. 15, in accordance with another embodiment a screw delivery system 810 includes a plurality of screw and driver assemblies 814 positioned in a carrier 818. Each assembly 814 includes a driver 822 pre-loaded with a screw 826. As shown, each driver 822 includes a coupling 830 at a proximal end and a driver head 834 at a distal end. As shown, a screw 822 is pre-loaded onto each driver head 834. The coupling 830 may be any coupling capable of securely holding a handle, and can be adapted to receive a standard handle or a battery powered handle. In the illustrated embodiment, the coupling 830 is a hex coupling adapted to fit into a hexagonal recess defined in a handle. In use, a handle may be engaged to a first assembly 814 and the first screw 822 may be applied to an underlying bone or other structure. Once the first screw 822 is in place the first driver 826 may be discarded, and the handle may be applied to a second assembly 814. This process may be repeated until the procedure is completed.

Figure 16A:
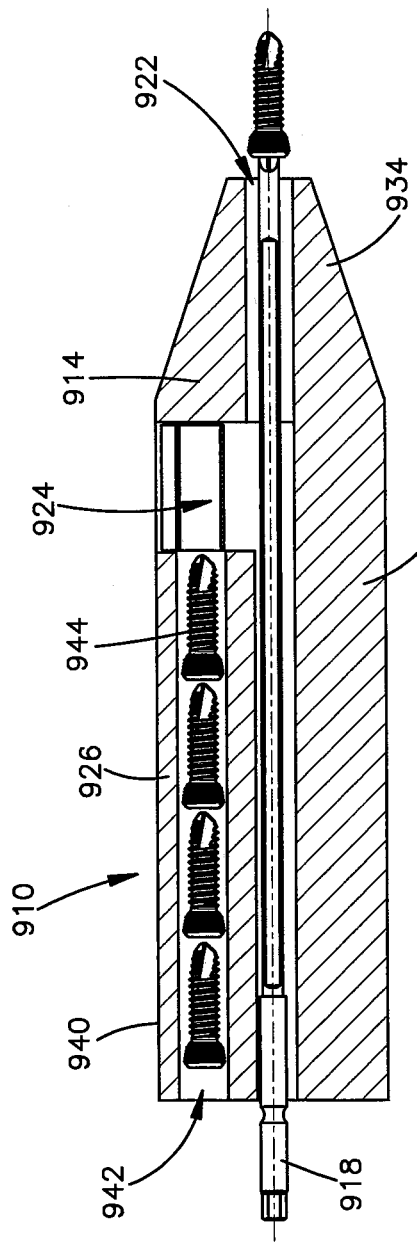
FIG. 16A is a schematic sectional side elevation view of a screw delivery system constructed in accordance with an another embodiment, the screw delivery system defining a channel that is configured to carry a plurality of fasteners, and a driver that is slidable within a bore disposed beneath the channel, and configured to individually engage each fastener disposed within the channel.
Figure 16B:
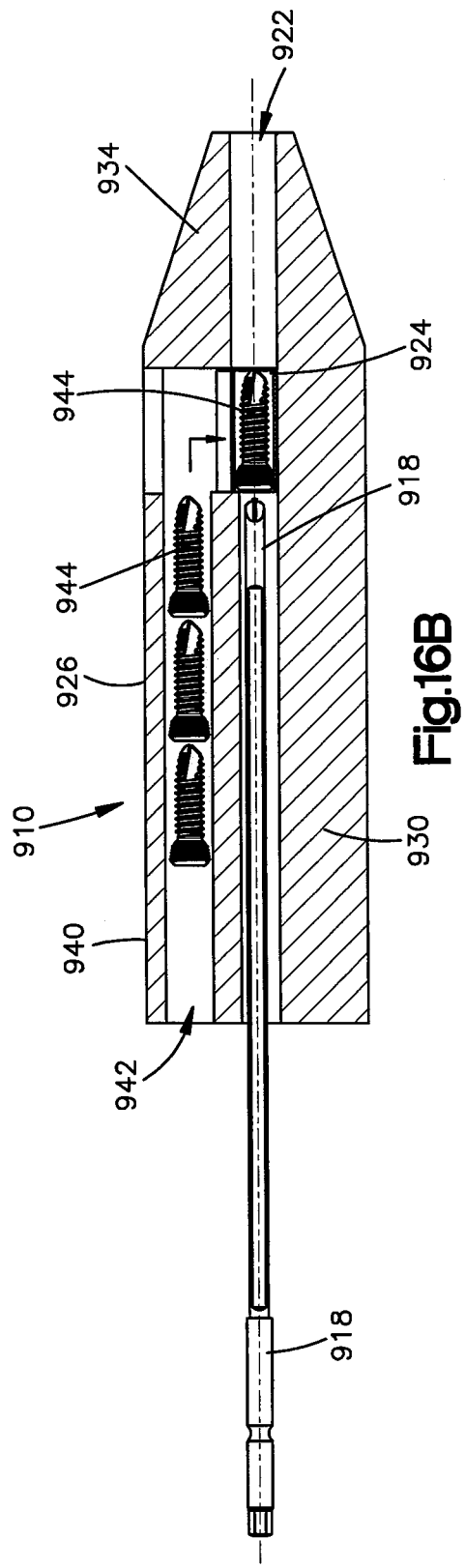
FIG. 16B is a schematic sectional side elevation view of the screw delivery system shown in FIG. 16A showing a screw loaded into the bore.

In reference to FIGS. 16A and 16B a screw delivery system 910 includes a body 914, a driver 918 extending through a bore 922 of the body 914, a screw carriage 924, and a linear screw cartridge 926 coupled to the body 914 and in communication with both the bore 922, and the screw carriage 924. The linear screw cartridge 926 is linear and holds screws 944 in a linear arrangement such that each screw lies one after another along a substantially linear direction. As shown, the body 914 includes a rear portion 930 and a front portion 934 coupled to the rear portion 930. The bore 922 extends through both the rear and front portions 930 and 934 of the body 914. The driver 918 is capable of slideably engaging and extending completely through the bore 922.

The screw cartridge 926 is attached to an upper surface of the body 914. The cartridge 926 is defined by a tubular body 940 that extends longitudinally along with the body 914. Tubular body 940 includes a tubular channel 942 that extends substantially along its length. As shown, a plurality of screws 944 are positioned linearly within the tubular channel 942 of the cartridge 926. Tubular body 940 includes an opening 950 at its distal end that is in communication with the screw carriage 924.

The screw carriage 924 includes a bore that extends therethrough and is capable of moving between an upper position and a lower position. In the upper position, the bore of the screw carriage 924 is aligned with the opening 950 of the cartridge 926. In the lower position, the bore of the screw carriage 924 is aligned with the bore 922 of the body 914. Therefore, the bore 922 of the body 914 may selectively receive each screw 944 when such a screw is to be driven into an underlying structure.

In use, the driver 918 may be pulled back, and a first screw 942 may be pushed through the tubular channel 942, out the opening 950, and into the carriage 924. The carriage 924 may then be pushed downward and into the bore 922. The driver 918 may then be pushed forward to thereby directly engage and advance the screw along the bore 922 and out of the body 914. Preferably, an alignment assembly, such as assembly 16, is utilized to help align the driver to the driving feature of the screw head. Once the first screw has been properly implanted, the driver 918 may then be retracted and the process may be repeated.

In reference to FIG. 17 the screw delivery system may include a plurality of pre-loaded drivers that are configured to rotate about a carrier such that each driver may be individually oriented to drive a pre-loaded fastener into tissue. As shown, a screw delivery system 1010 includes a carrier 1014, a driver 1018 extending through a bore 1022 of the carrier 1014, and a plurality of blade assemblies 1026 attached to the carrier 1014. The carrier 1014 includes a track 1030 that runs proximate to an outer surface of the carrier 1014. The track 1030 carries the blade assemblies 1026. Carrier 1014 also includes a larger bore 1034 that terminates into the bore 1022. The bore 1034 houses a spring 1038 that contacts and biases the driver 1018 in a forward direction.

The driver 1018 includes a base 1042 and a shaft 1046 extending from the base 1042. As shown in FIG. 17, the shaft 1046 extends through the bore 1022 of the carrier 1014, and the base 1042 abuts a surface 1050 to prevent the driver 1022 from falling out of the carrier 1014 when the driver 1018 is biased forward. Accordingly, the base 1042 has a diameter that is greater than both the external diameter of the shaft 1046 and the internal diameter of the bore 1022.

Each blade assembly 1026 includes a screw 1054 pre-loaded onto a driver head 1058. As shown, each driver head 1058 rides along the track 1030 and includes a recess 1062 defined in its bottom. The recesses 1062 should be sized to receive an end of the shaft 1046 as shown in FIG. 17.

In use, the driver 1018 may be pulled back, and a spring 1066 advances a first blade assembly 1026 toward an opening of the bore 1022. Once the blade assembly 1026 is in place, the driver 1018 may be released to allow the end of the shaft 1046 to engage the recess 1062 of the driver head 1058. Once, the first screw 1054 is implanted, the driver 1018 may be pulled back and a second blade assembly 1026 may be positioned to be implanted. This process may be repeated until the procedure is completed.

In reference to FIG. 18 the screw delivery system may include a plurality of blade assemblies that may be selectively employed. As shown, a screw delivery system 1110 includes a carrier 1114 and a plurality of blade assemblies 1118 housed within a cavity 1122 of the carrier 1114. The carrier 1114 includes a plurality of apertures 1126 defined in its outer walls and an opening 1128 at its distal end. In the illustrated embodiment, the system 1110 includes three assemblies 1118 housed within the cavity 1122.

Each blade assembly 1118 includes an elongate shaft 1130 having a head portion 1132 at its distal end and a depressible button 1134 at its proximal end. Each head portion 1132 has a screw 1140 pre-loaded onto it and each button 1134 extends out a respective aperture 1126 defined by the carrier 1114.

In use, a first button 1134 will be pushed down to advance a first assembly 1118 out of the opening 1128 to thereby expose a first screw 1140 to be implanted. After the first screw is implanted, the first assembly 1118 may be retracted and a second assembly 1118 may be employed to expose a second screw 1140 for implantation. This procedure may be repeated until all assemblies 1118 have been employed.

Although embodiments and their advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention. It will be appreciated by those skilled in the art that various modifications and alterations of the invention can be made without departing from the broad scope of the appended claims. Some of these have been discussed above and others will be apparent to those skilled in the art. Furthermore, the invention encompasses any combination of the features of any of the embodiments and natural variations thereof, as will be understood by persons familiar in the art.

Furthermore, it should be appreciated that the screw delivery systems disclosed may be provided as a kit includes one or more cartridges, alone or in combination with an alignment assembly, such as assembly 31, and further in combination with a driver such as driver 22. Each cartridge can retain screws having the same or different dimensions, such as the screw shaft diameter, screw length, and screw head configuration (e.g., flat, Phillips, hexagonal, or the like).

What is claimed:

1. A screw delivery system comprising:
   a carrier including a carrier body, the carrier defining a bore that extends at least partially through the carrier body;
   a driver configured to extend at least partially into the bore, the driver having a head that is configured to mate with a head of a fastener;
   at least a first guide member carried by the carrier body; and
   a nose operably aligned with the bore, the nose comprising at least a second guide member configured to engage the first guide member,
   wherein the nose is configured to receive a fastener such that as the driver is inserted from the bore into the nose the first and second guide members engage and the nose and fastener rotate relative to the carrier body.

2. The screw delivery system of claim 1, further comprising a fastener, wherein the driver pushers the fastener into the nose such that the nose and fastener rotate together relative to the carrier body.

3. The screw delivery system of claim 2, wherein rotation of the fastener and nose align the head of the fastener to the driver head as the driver pushes the fastener and nose forward.

4. The screw delivery system of claim 1, further comprising a guide body carried by the carrier body, the guide body carrying the first guide member.

5. The screw delivery system of claim 4, wherein the guide body is removably coupled to the carrier body.

6. The screw delivery system of claim 5, wherein the guide body comprises an end cap that is removably coupled to an end of the carrier body.

7. The screw delivery system of claim 1, wherein the carrier body defines a receptacle, that is configured to receive a cartridge having at least one fastener.

8. The screw delivery system of claim 7, further comprising a cartridge positioned within the receptacle of the carrier body, the cartridge having a plurality of fasteners therein.

9. The screw delivery system of claim 8, wherein the cartridge includes a cartridge body having a curved front face and a curved rear face.

10. The screw delivery system of claim 9, wherein the cartridge body defines a plurality of bores, each bore extends from the front face of the cartridge body and opens up to the rear face of the cartridge body, wherein a fastener is positioned within each bore.

11. The screw delivery system of claim 9, wherein the carrier includes a locking mechanism that is configured to selectively engage a corresponding locking mechanism defined by the cartridge.

12. The screw delivery system of claim 11, wherein (i) the locking mechanism of the cartridge is a plurality of detents defined in the curved rear face of the cartridge body, each detent being aligned with a respective bore, and (ii) the locking mechanism of the carrier is a spring loaded ball that is configured to selectively engage each detent.

13. The screw delivery system of claim 1, wherein the first guide member is a protrusion, and the second guide member is a helical groove.

14. The screw delivery system of claim 1, wherein the first guide member is a helical groove, and the second guide member is a protrusion.

15. The screw delivery system of claim 1, wherein the nose is configured to rotate at least 90 degrees relative to the carrier body.

16. The screw delivery system of claim 1, wherein the nose includes a nose body that defines a plurality of fingers, and a channel that extends through the nose body, wherein the fingers of the nose body are configured to flex outward as a fastener is being advanced through the channel.

17. The screw delivery system of claim 16, wherein each finger includes a non-linear proximal portion.

18. The screw delivery system of claim 17, wherein at least 1.5 lbs of force is required to force a fastener through the distal opening of nose body.

19. The screw delivery system of claim 16, wherein the nose body defines a distal opening that is in communication with the channel, the distal opening having a diameter that is less than the diameter of the fastener head.

20. A screw delivery system comprising:
- a carrier including a carrier body and defining a bore that extends at least partially through the carrier body, the carrier body configured to hold a plurality of fasteners; and
- a driver configured to be at least partially disposed in the bore, the driver having a head that is configured to mate with a head of a fastener; and
- a nose operably aligned with the bore
- wherein the bore is configured to selectively receive each fastener of the plurality of fasteners, and the nose is configured to cause relative rotation between the head of the driver and the fastener as the driver is advanced within the bore.

21. The screw delivery system of claim 20, further comprising at least a first guide member carried by the carrier body; and
- the nose includes at least a second guide member configured to engage the first guide member,
- wherein (i) the driver is configured to push a first fastener of the plurality of fasteners into the nose, such that the first fastener and nose rotate relative to the carrier body and align the head of the first fastener to the driver head as the driver pushes the screw and nose forward relative to the carrier body.

22. The screw delivery system of claim 21, further comprising a guide body carried by the carrier body, the guide body carrying the first guide member.

23. The screw delivery system of claim 22, wherein the guide body is removably coupled to the carrier body.

24. The screw delivery system of claim 23, wherein the guide body comprises an end cap that is removably coupled to an end of the carrier body.

25. The screw delivery system of claim 21, wherein the first guide member is a protrusion, and the second guide member is a helical groove.

26. The screw delivery system of claim 21, wherein the nose includes a nose body that defines a plurality of deflectable fingers, and a channel that extends therethrough, wherein the fingers of the nose body are configured to flex outward as a fastener is being advanced through the channel.

27. The screw delivery system of claim 20, further comprising a cartridge that initially holds the plurality of fasteners.

28. The screw delivery system of claim 27, wherein the carrier defines a front portion, a rear portion, and a receptacle disposed between the front and rear portions, the cartridge is configured to be disposed in the receptacle and rotatable relative to the front and rear portions about a transverse axis that is perpendicular to the bore that extends through the carrier.

29. The screw delivery system of claim 28, wherein (i) the cartridge includes a plurality of bores and a fastener of the plurality of fasteners is positioned in at least a majority of the bores, and (ii) the cartridge can be rotated to align each fastener with the driver so that the driver can retrieve and directly engage each fastener when each fastener is to be driven by the driver.

30. The screw delivery system of claim 20, wherein the head of the fastener is aligned to the head of the driver without rotating the driver.

31. The screw delivery system of claim 20, wherein (i) the carrier body includes a channel disposed above the bore and in communication with the bore, and (ii) the plurality of fasteners are aligned one after another within the channel.

32. The screw delivery system of claim 20, wherein rotation of the fastener as the driver is advanced within the bore causes the head of the driver to directly engage and mate with the head of the fastener.

33. The screw delivery system of claim 20, wherein rotation of the head of the driver as the driver is advanced within the bore causes the head of the driver to directly engage and mate with the head of the fastener.

34. A screw cartridge for a screw delivery system, the cartridge comprising:
- a cartridge body having a curved front face and an opposed curved rear face, and a pair of opposed side walls connected between the front and rear faces;
- a plurality of angular offset bores extending through the cartridge body from the front face of the body and opening up to the rear face; and
- a bone fastener positioned within at least a plurality of the bores.

35. The screw cartridge of claim 34, wherein the cartridge body includes a locking mechanism that is configured to be selectively engaged.

36. The screw cartridge of claim 35, wherein (i) the locking mechanism is a plurality of detents defined in the curved rear face of the cartridge body, each detent being aligned with a respective bore.

37. The screw cartridge of claim 35, wherein the locking mechanism is a plurality of teeth that are configured to be engaged by a ratchet.

38. The screw cartridge of claim 34, wherein the side walls are substantially flat.

39. The screw cartridge of claim 34, further comprising a capture device positioned within each bore, the capture device configured to hold a fastener.

40. A screw delivery system comprising:
- a carrier defining a front portion, a rear portion, a receptacle disposed between the front and rear portions, and a longitudinal bore that extends longitudinally through the front portion and the rear portion;
- a cartridge that is configured to be disposed in the receptacle and rotatable relative to the front and rear portions about a transverse axis that is perpendicular to the longitudinal bore, the cartridge includes a plurality of bores and a fastener positioned in at least a majority of the bores; and
- a driver configured to be at least partially disposed in the bore of the carrier, the driver having a head that is configured to mate with a head of each fastener, wherein the cartridge can be rotated to align each fastener with the driver so that the driver can retrieve and directly engage each fastener when each fastener is to be driven by the driver.

41. The screw delivery system of claim 40, wherein the longitudinal bore is configured to selectively receive each fastener, and relative rotation between the head of the driver and the fastener as the driver is advanced within the longitudinal bore causes the head of the driver to directly engage and mate with the head of the fastener when the fastener is to be driven.

42. The screw delivery system of claim 41, wherein rotation of the head of the driver as the driver is advanced within the bore causes the head of the driver to directly engage and mate with the head of the fastener.

43. The screw delivery system of claim 41, further comprising at least a first guide member carried by the carrier body; and
- a nose operably aligned with the bore, the nose comprising at least a second guide member configured to engage the first guide member,
- wherein (i) the driver is configured to push a fastener from the cartridge and into the nose, such that the fastener and nose rotate relative to the carrier body and align the head of the fastener to the driver head as the driver pushes the screw and nose forward relative to the carrier body.

44. A screw delivery system comprising:
- a carrier including a carrier body and defining a bore that extends at least partially through the carrier body, the carrier body configured to hold a plurality of fasteners; and
- a driver configured to be at least partially disposed in the bore, the driver having a head that is configured to mate with a head of a fastener,
- wherein the bore is configured to selectively receive each fastener of the plurality of fasteners, and advancement of the driver through the bore causes the head of the driver to rotate relative to the fastener so as to automatically align and mate the head of the driver with each fastener when each fastener is to be driven.

45. The screw delivery system of claim 44, wherein the driver includes a driving portion and an outer housing that defines a helical track, the driving portion includes a pin that mates with the helical track such that as the driver is advanced through the bore the outer housing collapses onto the driving portion and the pin follows the helical track to thereby rotate the driving portion.

46. The screw delivery system of claim 44, wherein the driver includes a driving portion and an outer housing that defines external threads, the carrier defines internal threads that mate with the external threads of the outer housing such that as the driver is advanced through the bore the threaded engagement between the outer housing and the carrier causes the driving portion to rotate.

* * * * *